US009332905B1

(12) United States Patent
Sims

(10) Patent No.: US 9,332,905 B1
(45) Date of Patent: *May 10, 2016

(54) DIAGNOSTIC METHOD AND SYSTEM FOR DETECTING EARLY AGE-RELATED MACULAR DEGENERATION, MACULOPATHIES AND CYSTOID MACULAR EDEMA POST CATARACT SURGERY

(71) Applicant: Clinton Norton Sims, Fort Myers, FL (US)

(72) Inventor: Clinton Norton Sims, Fort Myers, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/803,407

(22) Filed: Jul. 20, 2015

Related U.S. Application Data

(63) Continuation-in-part of application No. 14/618,360, filed on Feb. 10, 2015, now Pat. No. 9,144,379.

(51) Int. Cl.
*A61B 3/10* (2006.01)
*A61B 3/14* (2006.01)
*A61B 3/12* (2006.01)
*A61B 3/00* (2006.01)

(52) U.S. Cl.
CPC ............... *A61B 3/12* (2013.01); *A61B 3/0016* (2013.01); *A61B 3/0075* (2013.01); *A61B 2560/0223* (2013.01)

(58) Field of Classification Search
USPC .................................. 351/208, 218, 221, 246
See application file for complete search history.

(56) References Cited

U.S. PATENT DOCUMENTS

| 3,597,051 | A | 8/1971 | Copeland |
| 5,430,508 | A | 7/1995 | Sims |
| 5,500,698 | A | 3/1996 | Sims |
| 5,632,282 | A | 5/1997 | Hay et al. |
| 5,650,839 | A | 7/1997 | Sims |
| 6,578,965 | B2 | 6/2003 | Grant |
| 6,640,124 | B2 | 10/2003 | Elsner et al. |
| 7,467,870 | B2 | 12/2008 | van de Kraats et al. |
| 8,272,739 | B2 | 9/2012 | Sims |
| 8,272,740 | B2 | 9/2012 | Sims |
| 8,485,664 | B2 | 7/2013 | Rowe |
| 2008/0221416 | A1 | 9/2008 | Baker |
| 2014/0120112 | A1 | 5/2014 | Lashkari |

FOREIGN PATENT DOCUMENTS

CN          202458313          10/2012

OTHER PUBLICATIONS

Ferris, FL III, Wilkinson, CP, Bird A, et al. Clinial Calssification of Age-Related Macular Debeneraiton. Ophthalmology,2012, 844-851
Beatty S, Boulton M, Henson D, Koh Hh, Mu.

*Primary Examiner* — Jack Dinh
(74) *Attorney, Agent, or Firm* — Livingston Loeffler, P.A.; Edward M. Livingston, Esq; Bryan L. Loeffler, Esq.

(57) ABSTRACT

A retinoscopic device, technique and scale for estimating the reflectance of the macula pigment optical density (MPOD) in normal and abnormal eyes in order to detect early pathology of the retinal pigment epithelium and photoreceptors thus screening for macular pathology the most prevalent of which is Age-related Macular Degeneration (AMD) and retinal edema and cystoid macular edema post cataract surgery.

8 Claims, 22 Drawing Sheets

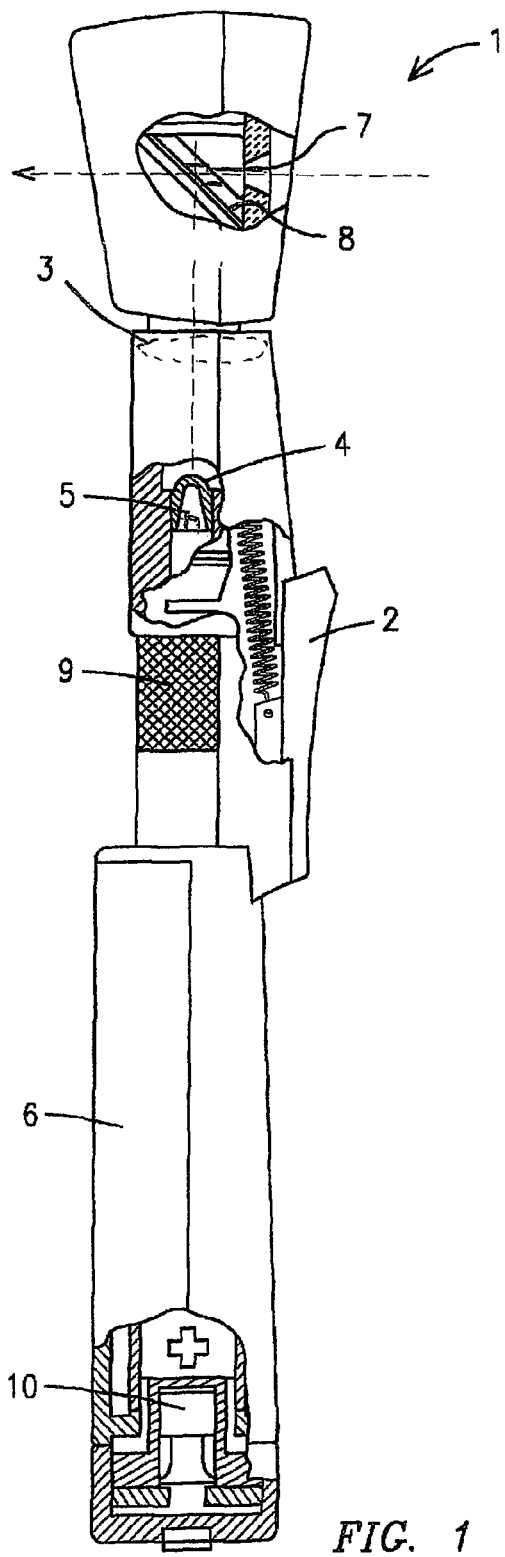
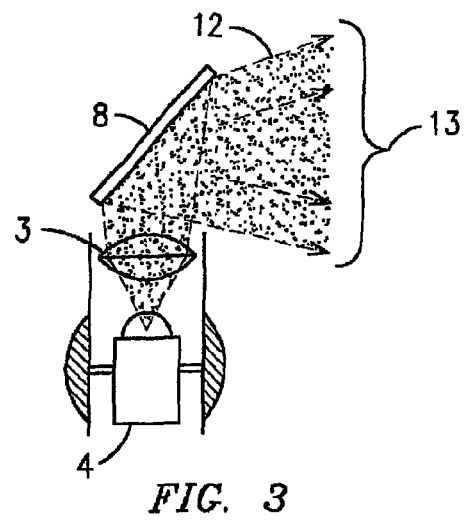
FIG. 3
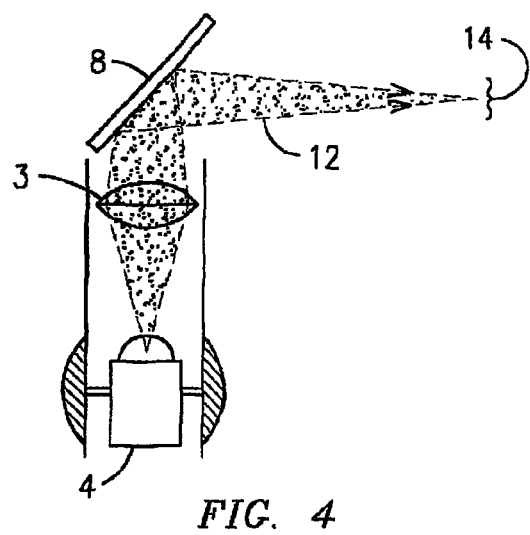
FIG. 4
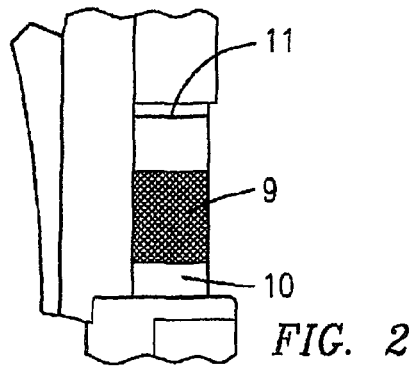
FIG. 1
FIG. 2

```
┌─────────────────────────────────────────────────────────────┐
│   Optical measurement of retinoscopic working distance:     │─15
│   Focus retinoscope into an emmetropic eye from one's       │
│   retinoscopic working distance until a neutrality reflex is seen. │
└─────────────────────────────────────────────────────────────┘
                              │
┌─────────────────────────────────────────────────────────────┐
│          Hold thumb-slide held in place and                 │─16
│        focus the retinoscopic streak onto a wall.           │
└─────────────────────────────────────────────────────────────┘
                              │
┌─────────────────────────────────────────────────────────────┐
│      Measure the distance between the retinoscope and wall. │─17
└─────────────────────────────────────────────────────────────┘
```

*FIG. 5*

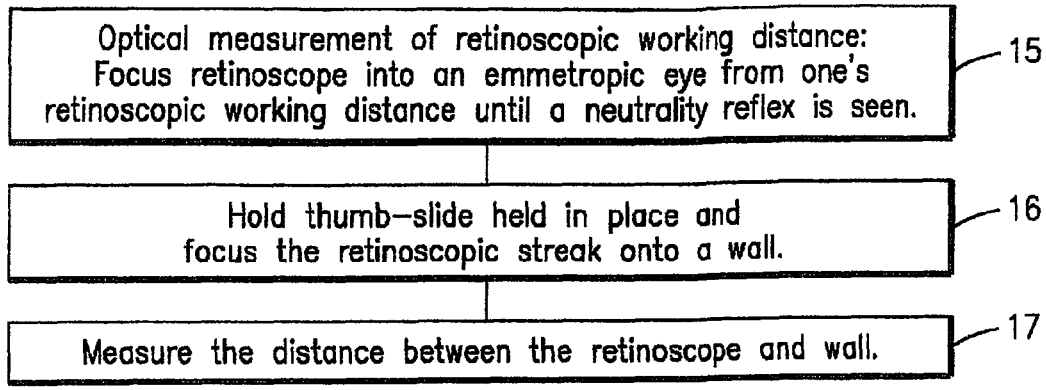

| Retinoscopic Working Distance (cm) | Sphere Power Required to Calibrate Retinoscope Retinoscope Using Diverging Light (D) | | Required Focal Length of Retinoscopic Light to Calibrate Retinoscope for Converging Infinity Retinoscopy (cm) | |
|---|---|---|---|---|
| | Infinity Retinoscopic Endpoint | +0.50D Retinoscopic Endpoint | +0.50D Retinoscopic Endpoint | +0.75D Retinoscopic Endpoint |
| 50 | +4.00 | +4.50 | 67 | 80 |
| 54 | +3.75 | +4.25 | 73 | 89 |
| 57 | +3.50 | +4.00 | 80 | 100 |
| 62 | +3.25 | +3.75 | 89 | 115 |
| 67 | +3.00 | +3.50 | 100 | 133 |
| 73 | +2.75 | +3.25 | 115 | 161 |
| 80 | +2.50 | +3.00 | 133 | 200 |

Table 1. Five-Year Rate of Developing Advanced AMD in AREDS Participants by Drusen Size and Degree of Pigmentary Abnormalities

| Drusen Size | Pigmentary Abnormalities None | Pigmentary Abnormalities One Eye | Pigmentary Abnormalities Both Eyes |
|---|---|---|---|
| None or small drusen | 0.4% (4/1017) | 0% (0/64) | 12.5% (1/8) |
| Intermediate drusen one eye no large drusen | 0.5% (2/449) | 5.0% (5/101) | 12.9% (4/31) |
| Intermediate drusen both eyes no large drusen | 2.1% (4/187) | 12% (6/50) | 20% (7/35) |
| Large drusen one eye | 3.9% (11/283) | 10.1% (17/168) | 25.6% (30/117) |
| Large drusen both eyes | 13% (27/208) | 27.3% (48/176) | 47.3% (150/317) |

AMD = age-related macular degeneration; AREDS = Age-Related Eye Disease Study.

FIG. 16

| Brightness Scale | Brightness of Pupillary Streak | Diagnosis |
|---|---|---|
| #4 | BRIGHT, DISTINCT PUPILLARY STREAK | YOUNG HEALTHY EYE |
| #3 | SLIGHTLY LESS BRIGHT AND LESS DISTINCT PUPILLARY STREAK | OLDER HEALTHY EYE |
| #2 | MODERATE REDUCTION OF BRIGHTNESS OF PUPILLARY STREAK | PROBABLE MACULAR PATHOLOGY |
| #1 | FAINT PUPILLARY STREAK | MODERATE TO ADVANCED AMD |
| #0 | NO PUPILLARY STREAK | ADVANCED AMD |

| Power of the pupillary reflex ($I_3$) | Focal length of the pupillary reflex (cm) | Decrease of the light intensity of the pupillary reflex |
|---|---|---|
| +1.50D | 67 | 0.01 |
| +1.00D | 100 | 1.00 |
| +0.75D | 133 | 2.00 |
| +0.62D | 161 | 3.00 |
| +0.50D | 200 | 4.00 |

FIG. 25

DIAGNOSTIC METHOD AND SYSTEM FOR DETECTING EARLY AGE-RELATED MACULAR DEGENERATION, MACULOPATHIES AND CYSTOID MACULAR EDEMA POST CATARACT SURGERY

CROSS-REFERENCE TO RELATED APPLICATIONS

This application is a continuation-in-part of application Ser. No. 14/618,360, filed on Feb. 10, 2015, which is currently pending. The patent application identified above is incorporated herein by reference in its entirety to provide continuity of disclosure.

FIELD OF THE INVENTION

This invention relates to a method and system for using a calibrated retinoscope and parallel light technique to estimate the reflection of melanin particles in the retina to detect macular degeneration prior to physical symptoms.

BACKGROUND OF THE INVENTION

In the Western world, maculopathy or AMD is the leading cause of blindness in the elderly population and affects 10%-13% of adults over 65 in North America, Europe, Australia and Asia In 2012 the undiagnosed prevalence of AMD in the USA was estimated to be 2.3 million. Estimates of the global cost due to AMD are US$343 billion with US$255 billion in direct health care costs.

According to the International Classification age-related maculopathy (ARM) is a degenerative disease of the macula characterized in the early stage by large, soft yellow drusens, hyper-/hypopigmentation of the retinal pigment epithelium (RPE), and a moderate loss of central vision (age-related maculopathy). Age related maculopathy disease (AMD) is a late stage of ARM. Dry AMD refers to geographic atrophy and wet AMD is characterized by choroidal neovascularization (CNV), detachment of the RPE, subretinal hemorrhage or retinal scarring.

Currently, several AMD classification schemes, grading systems, and severity scales have been developed in an effort to provide standards to assist clinicians and researchers in the diagnosis and management of this important disorder. The most current clinical classification of AMD takes in consideration pigment abnormalities and is illustrated in FIG. 16.

It is believed the ultimate therapy for AMD will lie in the preclinical identification of those who are genetically "at risk" for the disease and treatment with genetically specific supplements. At the present time, AMD is initially diagnosed by an ophthalmologist or optometrist with a fundus examination and Amsler grid of patients who complain of a decrease in their vision. The hallmarks of early AMD are yellow drusens and pigment abnormalities (hypo and hyper-pigmentation) of the retinal pigment epithelium (RPE) which occur after the onset of the AMD process. AMD is characterized by a degeneration of the retinal pigment epithelium and photoreceptors (rod and cones) and a thickening of the Bruch's membrane in the macula.

The early detection of AMR could reduce the growing societal burden by targeting and emphasizing modifiable habits earlier in life. With genetic testing antioxidants and other supplements specific to the patient's genotype can be recommended. More frequent examinations of those at high risk due to family history or signs of early or intermediate disease would be beneficial.

It is believed that the pigmentary changes observed in the macula of AMD eyes are attributable to degenerative changes in the highly melanized RPE cells because most of the early clinical signs and histopathological changes have been localized to this cell layer. It has been suggested that melanin in the retinal pigment epithelium (RPE) and choroid may protect the macular region by its antioxidant capability and its capability to attenuate or reflect light thereby decreasing photochemical light damage.

In retinoscopy, a light is shone into a patient's eye and the reflected "streak" of light is used to estimate the correction of a patient's refractive error. The results are then the beginning point for a refraction. However, with the calibrated retinoscope and this technique, the brightness of the reflected beam is dependent on the health of the pigment epithelium and thus gives an early indication of macular pathology. This calibrated diagnostic retinoscope and technique allow the general ophthalmic physician to detect early and late stages of the destruction of the retinal pigment epithelium in AMD. The common denominator between AMD and the pupillary reflex in retinoscopy lies in the melanin pigment particles of the microvilli of the retinal pigment epithelium (RPE) which surrounds the photoreceptors, the choroid and/or the outer segment of the cones.

In 1926, Jacob C Copeland designed a retinoscope (U.S. Pat. No. 3,597,051) and a technique of retinoscopy which has since been taught to optometrists and ophthalmologists for obtaining an objective measurement of the refractive error of patient's eyes for spectacles and/or contact lenses. All retinoscopes have been based upon on his work.

Originally, Copeland's and other retinoscopes used diverging light and spots of light to estimate the refractive error. Copeland introduced streak retinoscopy in the US and it was rapidly accepted because it made determination of the axis of astigmatism more precise. The technique was referred to as "streak retinoscopy" because a streak of reflected light, or the pupillary reflex, was produced during the technique.

In 1968, Copeland and Walter M. Lewis designed the Copeland Optec 360 Streak Retinoscope, U.S. Pat. No. 3,597,051 (as illustrated in FIG. 17). This retinoscope contains a +20.00 D condensing lens and a bi-pin filament bulb. When the thumb-slide is in its upper position, the filament of the lamp is less than five centimeters from the condensing lens and the rays emanating from the filament and passing out of the condensing lens are diverging. Moving the thumb-slide to a lower position causes the light rays to converge. When the filament is at the focal point of the +20.00 D lens or approximately 5 cm from the +20.00 D lens, the light rays are parallel.

Sims' calibrated refractive retinoscopic techniques uses converging rather than diverging light. The Sims' retinoscope can also be used for calibrated diverging or conventional diverging retinoscopic techniques. It has been modified so that auxiliary lenses can be attached to the back of the head of the retinoscope to place the examiner's eye in focus with the patient's pupillary plane in order to have an identical (conjugate) image of the pupillary reflex. Parallel light is used after the refractive error has been determined to judge the streak on a reflectance scale 0 (very poor and difuse) to 4 (brilliant).

In conventional retinoscopy, the pupillary reflex cannot be used to evaluate the melanin reflectance. The endpoint of conventional retinoscopy is an infinity neutrality reflex which fills the pupil and there is no streak. The width of the reflected retinoscopic light from the reflecting membrane spans an area much larger than the size of the pupil and is enormous, making it impossible to evaluate the reflectance of the macular pigment (MP). With conventional retinoscopy, the refractive error is initially determined by under correcting the refractive error to create a visible with-motion pupillary streak reflex that expands and moves at an exponentially increasing speed as neutrality is reached. These exponential changes of the with-motion streak makes it impossible to evaluate the reflectance of the MP.

Production of the Pupillary Reflex:

The cones act as an optical waveguide for visible light due to their tubular structure and the index gradient between the cell wall and internal medium. Since the cone's receptors are tightly packed, they act as a "fiber optic plate" extending from the external limiting membrane to the pigment epithelium (as illustrated in FIG. 18). Therefore light, that strikes the outer limiting membrane located at the openings of the photoreceptors, is transmitted to the photosensitive pigment in the outer segments by a waveguide mechanism and then reflected to the outer limiting membrane.

The reflected light from the retina pigment epithelium (RPE) interface appears to be due to Fresnel reflection from the melanin granules within the melanosomes in the RPE. A Fresnel reflection is a reflection of light on a planar interface between two homogeneous media having different refractive indices. The melanin granules in the pigment epithelium have a high index of refraction compared to the surrounding tissue. The reflected light then reenters the photoreceptors and transmitted to the external limiting membrane (ELM) and pupil. The ELM is considered the effective ocular reflecting surface for visible light in the performance of retinoscopy or photorefraction. Conventionally, the pupillary reflex is used to measure or estimate a refractive error, not to evaluate the reflectance from the melanin pigment.

Macular Degeneration and Reflectance:

Most of the early clinical signs and histopathological changes have been localized to the pigment epithelium. It is believed that it is the melanin in the retinal pigment epithelium (RPE) and choroid which protects the macular region through its antioxidant capability and its capability to attenuate blur light thereby decreasing photochemical light damage. Healthy pigment epithelium is more reflective than that which is damaged and when evaluated produces a brilliant to clear streak.

The calibrated retinoscope and diagnostic technique described in this patent application allows the average ophthalmic physician to detect early and late stages of the destruction of the retinal pigment epithelium in AMD.

The relevant prior art includes the following references:

| U.S. Pat. No. | Inventor | Issue/Publication Date |
| --- | --- | --- |
| 3,597,051 | Copeland | Aug. 3, 1971 |
| 5,430,508 | Sims | Jul. 4, 1995 |
| 5,500,698 | Sims | Mar. 19, 1996 |
| 5,632,282 | Hay et al. | May 27, 1997 |
| 5,650,839 | Sims | Jul. 22, 1997 |
| 6,578,965 | Grant | Jun. 17, 2003 |
| 6,640,124 | Elsner et al. | Oct. 28, 2003 |
| 2008/0221416 | Baker | Sep. 11, 2008 |
| 7,467,870 | van de Kraats et al. | Dec. 23, 2008 |
| 8,272,739 | Sims | Sep. 25, 2012 |
| 8,272,740 | Sims | Sep. 25, 2012 |
| 8,485,664 | Rowe | Jul. 16, 2013 |
| 2014/0140112 | Lashkari | May 1, 2014 |
| CN202458313 | Zhang | Oct. 3, 2012 |

(Non-Patent Literature)

Ferris, F L III, Wilkinson, C P, Bird A, et al. CLINIAL CALSSIFICATION OF AGE-RELATED MACULAR DEBENERAITON. Ophthalmology, 2012, 844-851 Beatty S, Boulton M, Henson D, Koh H H, Murray I J (1999) Macular pigment and age related macular degeneration. Br J Ophthalmol 83:867-77

SUMMARY OF THE INVENTION

The primary object of the present invention is to improve the detection of age-related maculopathies (ARM & AMD) other maculopathies and cystoid macular edema post cataract surgery using a modified retinoscope.

An additional object of the present invention is to provide a retinoscope capable of performing several calibrated refractive and diagnostic retinoscopic techniques and conventional retinoscopy.

The present invention fulfills the above and other objects by providing a retinoscopic device, technique and scale for estimating the reflectance of the macula pigment optical density (MPOD) in normal and abnormal eyes in order to detect early pathology of the retinal pigment epithelium and photoreceptors thus screening for macular pathology, the most prevalent of which is Age-related Macular Degeneration (AMD).

The retinoscopic device of the present invention is a calibrated, converging light retinoscope which improves the accuracy of retinoscopy by calibrating a pupillary streak to the vergence of the retinoscopic light and the retinoscopic working distance. This technique predicts the final correction so closely, it is referred to as "Refractive Retinoscopy".

An improvement of the present invention adds a technique using parallel light which enables an examiner to use a subjective scale or the "Primary Scale" to evaluate the pupillary streak to scan for Age-related Macular Degeneration (AMD). The pupillary streak produced by retinoscopy of a healthy eye differs from that produced in an eye with Age Related Macular Degeneration (AMD). The Primary Scale, requires the examiner to make an initial judgment as to the brightness of the pupillary streak produced by parallel light from one's retinoscopic working distance (RWD). This technique is referred to as "Diagnostic Retinoscopy" since it detects early AMD and the various progressive stages of AMD.

A more objective scale or the "Optical Scale" involves reducing the intensity of the chosen pupillary streak by increasing the focal length of the converging retinoscopic light. A healthy eye will be able to reflect a pupillary streak even when the light intensity of the pupillary reflex is maximally decreased. An eye with AMD pathology will cease reflecting a pupillary streak commensurate to the degree of macular damage. The advantage of the Optical Scale is it is easier to judge when the pupillary streak disappears than to make a subjective judgement of the brightness of the pupillary streak using the Primary Scale.

Although the device for carrying out the method and system described herein is optical and manual, the method and system of the present invention may also be used with an electronic instrument with a continuous scale much like a rheostat which could measure the optical scale even more precisely.

With continued use of the method and system of the present invention, it would be possible to establish a continuous scale probabilities of having macular problems which would correlate to the Optical Scale.

The above and other objects, features and advantages of the present invention should become even more readily apparent to those skilled in the art upon a reading of the following detailed description in conjunction with the drawings shown and the described illustrative embodiments of the invention.

BRIEF DESCRIPTION OF THE DRAWINGS

In the following detailed description, reference will be made to the attached drawings in which:

FIG. 1 is a side partial cutaway view of a condensing lens, a mirror, a lamp, a power capsule with a knurl for rotating the power capsule and a thumb-slide which moves the power capsule housing the lamp;

FIG. 2 is a schematic of the knurl area on the power capsule with a circumferential calibration line;

FIG. 3 is a schematic view of light rays emanating from a retinoscope in a diverging pattern;

FIG. 4 is a schematic view of light rays emanating from a retinoscope in a converging pattern;

FIG. 5 is a flow chart for optically measuring one's retinoscopic working distance;

FIG. 6 is a chart for calibrating the retinoscope using diverging rays for an infinity retinoscopic and +0.50 D endpoints and for calibrating a retinoscope using converging rays for +0.50 D and +0.75 D retinoscopic endpoints;

FIG. 7-B is an attachable plate for retrofitting a retinoscope for a +0.75 D retinoscopic endpoint using converging rays calibrated to the examiner's retinoscopic working distance;

FIG. 7-C is an attachable plate for retrofitting a retinoscope for an infinity retinoscopic endpoint using diverging rays calibrated to the examiner's retinoscopic working distance;

FIG. 7-D is an attachable plate for retrofitting a retinoscope for a +0.50 D retinoscopic endpoint using diverging rays calibrated to the examiner's retinoscopic working distance;

FIG. 8-A is a retinoscope showing proper attachment of the +0.50 D converging plate after calibration of retinoscope light rays to the examiner's retinoscopic working distance;

FIG. 9-A is a retinoscope showing proper attachment of the +0.75 D converging plate after calibration of retinoscopic light rays to the examiner's retinoscopic working distance;

FIG. 10-A is a retinoscope showing proper attachment of the infinity diverging plate after calibration of the retinoscopic light rays to the examiner's retinoscopic working distance;

FIG. 11-A is a retinoscope showing the proper attachment of the +0.50 D diverging plate after calibration of retinoscopic light rays to the examiner's retinoscopic working distance;

FIG. 16 is a chart showing the clinical classification of age-related macular degeneration;

FIG. 22 is a primary scale for detection of RPE maculopathy and age-related maculopathy or degeneration (AMD);

FIG. 25 is a chart illustrating the focal lengths of the pupillary reflex and the decrease in the light intensity of the pupillary reflex for a retinoscopic working distance (RWD) of 67 cm which is the most common RWD.

DESCRIPTION OF THE PREFERRED EMBODIMENTS

Figure 7A:
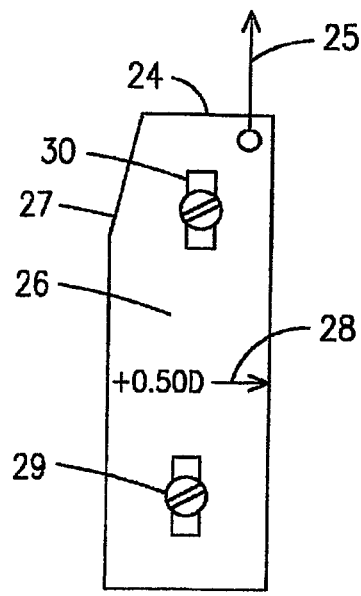
FIG. 7-A is an attachable plate for retrofitting a retinoscope for a +0.50 D retinoscopic endpoint using converging rays calibrated to the examiner's retinoscopic working distance.
Figure 7B:
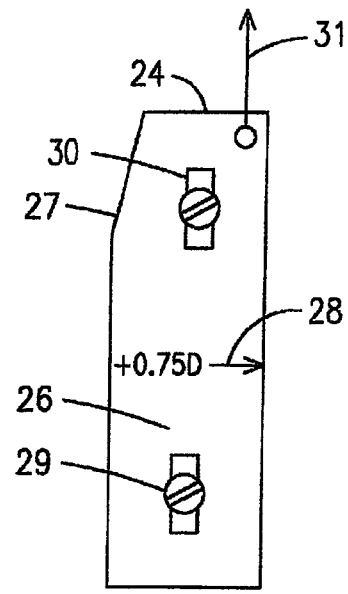
Figure 7C:
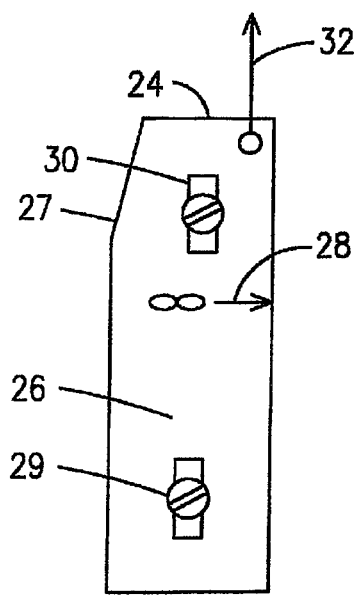
Figure 7D:
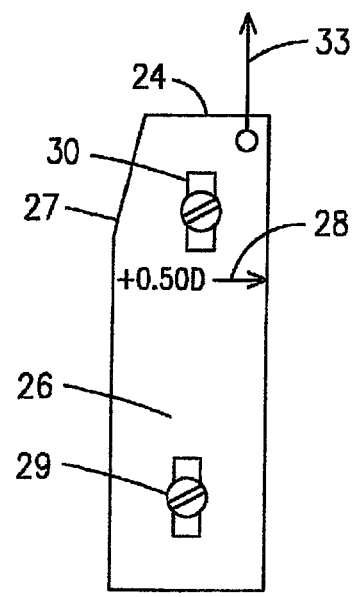

With reference to FIG. 1, a side partial cutaway view of a retinoscope 1 having a thumb-slide 2 and a condensing lens 3 and a lamp 4 is shown. The lamp 4 includes a linear filament 5 designed to create a "streak" image which is reflected from a patient's retina and seen by a practitioner, such as an optometrist or ophthalmologist. The thumb-slide 2 moves the power capsule housing the lamp 4 moves up and down along a handle of the retinoscope 6 so that when the thumb-slide 2 is in a maximal upward position, the filament 5 is less than 5 cm from lens 3 which has an approximate power of +20.00 D. When the thumb-slide 2 is in a maximal down position, the filament 5 is approximately 6.6 cm from the lamp 4. The practitioner can view the light rays reflected from the patient's retina through a small openings 7 in mirror 8 and head of retinoscope. The examiner can only see the retinoscopic light on the patient's iris and the reflected pupillary reflex. The examiner nevertheless is able to move the pupillary reflex toward neutralization by the movement and orientation of the pupillary reflex. The examiner draws all of the retinoscopic signals from the pupillary reflex, that is, when to change or rotate the retinoscopic streak to achieve neutralization of the spherical and cylindrical error.

With reference to FIG. 2, calibration of the retinoscope requires a calibration line 11 in the knurl area 9 on the power capsule 10 to align the Plates 7A and 7B for converging infinity retinoscopy and Plates 7C and 7D for diverging retinoscopy after the retinoscope is calibrated to the specifications in the Calibration Chart 18, as illustrated in FIG. 6.

With reference to FIG. 3, a schematic view of light rays 12 emanating from a retinoscope 1 in a diverging pattern 13 is shown. In diverging retinoscopy the lamp 4 is within the focal length of lens 3. The proximity of the lamp 4 to the lens 3 causes the light rays 12 emitted from the retinoscope 1 to spread out into a diverging pattern 13.

The retinoscopic technique of identifying and neutralizing a refractive error is the same with calibrated diverging retinoscopy as with conventional retinoscopy. Calibrated diverging retinoscopy differs from conventional retinoscopy in that the divergence of the emitted retinoscopic light rays 12 is calibrated to a fogging lens whose focal length is equal to one's retinoscopic working distance. The endpoint of calibrated diverging retinoscopy can be an infinity retinoscopic endpoint which is identical to the endpoint of conventional retinoscopy or a +0.50 D with-motion pupillary reflex.

With reference to FIG. 4, a schematic view of light rays 12 emanating from a retinoscope 1 in a converging pattern 14 is shown. In converging retinoscopy, the lamp 4 is displaced beyond the focal length of lens 3. The increased distance of the lamp 4 from the lens 3 causes the light rays 12 emitted from the retinoscope 1 to focus into a converging pattern 14.

With reference to FIG. 5, a flow chart showing the steps for measuring a retinoscopic working distance for use in calibrating a retinoscope for converging and diverging retinoscopy is shown. The examiner's retinoscopic working distance is optically measured by focusing the retinoscopic light into an emmetropic eye using the thumb slide until a neutrality reflex occurs 15. Then, the retinoscopist holds the thumb-slide on the retinoscope in place and the emitted retinoscopic light is focused onto a wall by moving the retinoscope towards the wall until the streak is in focus 16. Finally, the distance between the wall and retinoscope is measured to obtain the examiner's retinoscopic working distance 17.

With reference to FIG. 6, a calibration chart 18 is shown. The calibration chart 18 lists the retinoscopic working distance in centimeters 19 and the required power of the calibration lens to be held in front of the retinoscope, which is displaced from a wall a distance equal to the examiner's retinoscopic working distance 19, in order to calibrated the diverging retinoscopic light for an infinity endpoint 20 and a +0.50 D endpoint 21. Chart 18 also lists the distance a retinoscope must be held from a wall to calibrated the retinoscope using converging light for a +0.50 D endpoint 22 and a +0.75 D endpoint 23, when performing retinoscopy from one's retinoscopic working distance.

With reference to FIG. 7-A, an attachable plate 24 for retrofitting a retinoscope 1 when calibrated for a +0.50 D with-motion endpoint pupillary reflex using converging rays 14 emitted from the retinoscope 1 is shown. The plate 24 shown here is a +0.50 D converging plate 25 and is used when the converging light emanating from the retinoscopies is calibrated for a +0.50 D with-motion retinoscopic endpoint, as shown further in FIG. 8-A. The +0.50 D converging plate 25 has a front surface 26, a rear surface 27 and an alignment line 28. The plate 24 is attachable to the retinoscope via an attachment means 29, such as screws nuts, etc. The plate 24 is moveable via an adjustment means 30, such as a slot that moves along a screw, so that a user may adjust the alignment line 28 up or down to be in alignment with the calibration line 11 on the power capsule 10. After the retinoscope is calibrated and plate 24 secured into position, the alignment line 28 on plate 24 allows the retinoscopist to know where to place the calibration line 11 on the power capsule 10 to obtain a +0.50 D retinoscopic endpoint using converging light, as shown further in FIG. 8-A.

Figure 9:
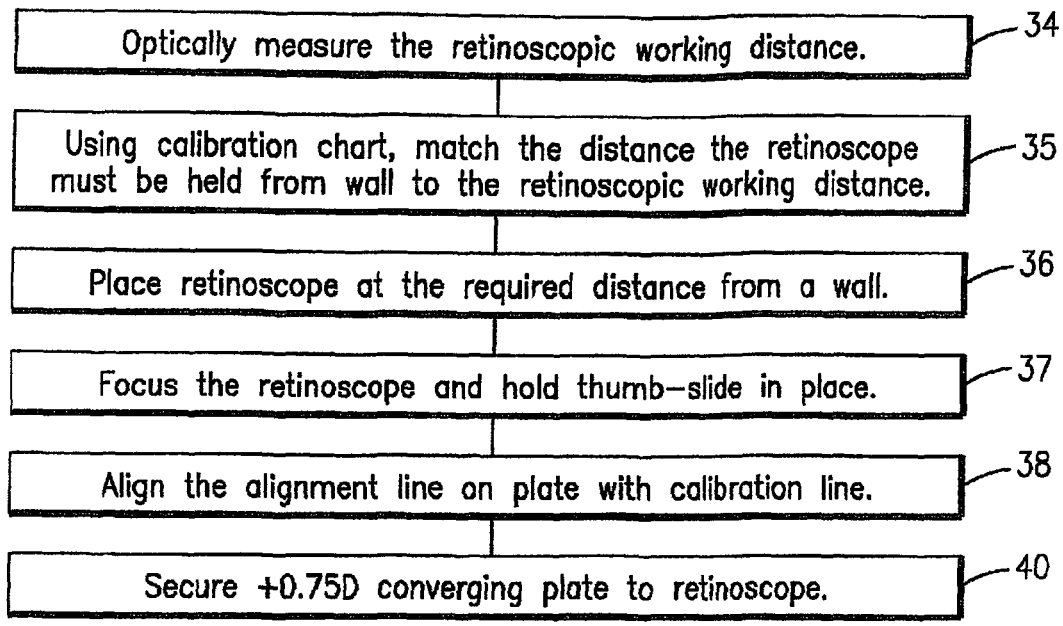

With reference to FIG. 7-B, an attachable plate 24 for retrofitting a retinoscope 1 when calibrated for a +0.75 D with-motion retinoscopic reflex using converging light rays 14 emitted from the retinoscope 1 is shown. The plate 24 shown here is a +0.75 D converging plate 31 and is used when the converging light 14 emanating from the retinoscope is calibrated for a +0.75 D with-motion retinoscopic endpoint, as shown further in FIG. 9-A. The +0.75 D converging plate 31 has a front surface 26, a rear surface 27 and an alignment line 28. The plate 24 is attachable to the retinoscope via an attachment means 29, such as screws nuts, etc. The plate 24 is moveable via an adjustment means 30, such as a slot that moves along a screw, so that a user may adjust the alignment line 28 up or down to be in level with the calibration line 11 on the power capsule 10. After the retinoscope is calibrated, as illustrated in FIG. 9, and plate 24 secured into position, the alignment line 28 on plate 31 allows the retinoscopist to know where to place the calibration line 11 on the power capsule 10 to obtain a +0.75 D retinoscopic endpoint using converging light, as shown further in FIG. 9-A.

With reference to FIG. 7-C, an attachable plate 24 for retrofitting a retinoscope 1 when calibrated for an infinity endpoint using diverging light rays 13 emitted from the retinoscope 1 is shown. The plate 24 shown here is an infinity endpoint diverging plate 32 and is used when the diverging light 13 emitted from the retinoscope is calibrated for an infinity retinoscopic endpoint, as shown further in FIG. 10 and FIG. 10-A. The infinity diverging plate 32 has a front surface 26, a rear surface 27 and an alignment line 28. The plate 24 is attachable to the retinoscope via an attachment means 29 such as screws, adhesive, nuts, etc. The plate 24 is moveable via an adjustment means 30, such as a slot that moves along a screw, so that a user may adjust the alignment line 28 up or down to be level with the calibration line 11 on the power capsule 10 after the retinoscope is calibrated. After the retinoscope is calibrated and plate 32 secured into position, the alignment line 28 on plate 32 allows the retinoscopist to know where to place the calibration line 11 on the power capsule 10 to perform retinoscopy with diverging light rays to obtain an infinity retinoscopic endpoint adjusted to one retinoscopic working distance as shown further in FIG. 10-A.

With reference to FIG. 7-D, an attachable plate 24 for retrofitting a retinoscope 1 when calibrated to a +0.50 D with-motion pupillary reflex endpoint using diverging retinoscopic light rays 13 is shown. The plate 24 shown here is a diverging plate 33 and is used when the diverging light emanating from the retinoscope is calibrated for a +0.50 D with motion retinoscopic endpoint as shown further in FIG. 11 and FIG. 11-A. The +0.50 D diverging plate 33 has a front surface 26, a rear surface 27 and an alignment line 28. The plate 24 is attachable to the retinoscope via an attachment means 29, such as screws, adhesive, nuts, etc. The plate 24 is moveable via an adjustment means 30, such as a slot that moves along a screw, so that a user may adjust the alignment line 28 up or down to be in alignment with the calibration line 11 on the power capsule 10 after the retinoscope is calibrated. The alignment line 28 on plate 33 allows the retinoscopist to know where to place the calibration line 11 on the power capsule 10 to perform retinoscopy with diverging light rays to obtain a +0.50 D retinoscopic endpoint adjusted to one retinoscopic working distance as shown further in FIG. 11-A.

Figure 8:
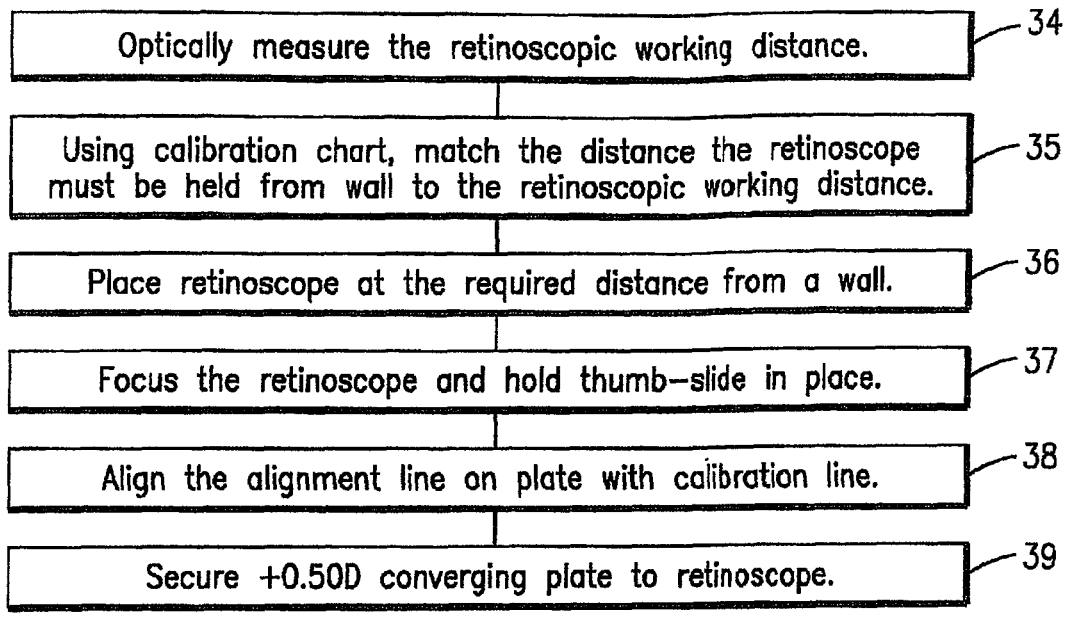
FIG. 8 is a flow chart showing the steps for calibrating a retinoscope for a +0.50 D retinoscopic endpoint using converging retinoscopic light rays calibrated to the examiner's retinoscopic working distance.
Figures 8A, 9A:
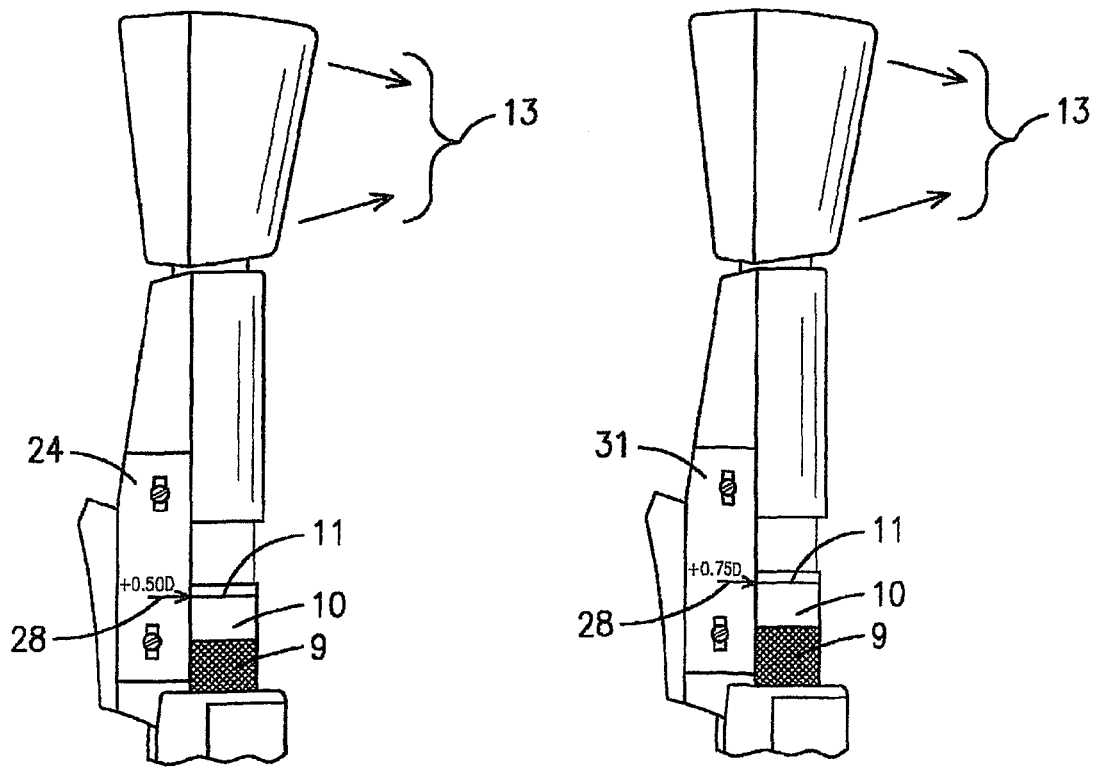
FIG. 9 is a flow chart showing the steps for calibrating a retinoscope for a +0.75 D pupillary reflex endpoint using converging retinoscopic light rays.

With reference to FIG. 8, a flow chart showing the steps for calibrating a retinoscope for a +0.50 D with-motions retinoscopic endpoint using converging retinoscope light rays 14 is show. First, the retinoscopic working distance is optically measured 34 as shown in FIG. 5. Then, the required focal length of the emitted retinoscope light for a +0.50 D retinoscopic endpoint is determined 35 using the calibration chart 18 illustrated in FIG. 6. For example, if the retinoscopic working distance is 67 cm, the required focal length of the emitted retinoscopic light is 100 cm. Next, the retinoscope is placed at the proper focal length from a wall 36 and focused 37. Finally 38, the alignment line 28 on the +0.50 D converging plate 25 is aligned with the calibration line 11 on the power capsule 10 as shown further in FIG. 8-A and secured 39.

With reference to FIG. 8-A, a retinoscope 1 having a +0.50 D converging plate 25 attached thereto is shown. The retinoscope 1 has been calibrated for a +0.50 D pupillary reflex endpoint using converging retinoscope light rays 14. The technique for performing retinoscope using a retinoscope calibrated for a +0.50 D retinoscopic endpoint is the same as in conventional retinoscopy, except that the calibration line 11 on the power capsule 10 is aligned with the alignment line 28 on the +050 D converging plate 25 and the retinoscopic endpoint is a +0.50 D with-motion retinoscopic reflex with the +0.50 D pupillary reflex and intercept moving in unison.

With reference to FIG. 9, a flow chart showing the steps for calibrating a retinoscope for a +0.75 D with-motions retinoscopic endpoint using converging retinoscope light rays 14 is show. First, the retinoscopic working distance is measured 34 as shown in FIG. 5. Then, the required focal length of the emitted retinoscope light is determined 35 using the calibration chart 18 illustrated in FIG. 6. For example, if the retinoscopic working distance is 67 cm, the required focal length of the emitted retinoscopic light is 133 cm. Next, the retinoscope is placed at the proper focal length from a wall 36 and focused 37 and the thumb-slide held in position. Finally 38, the alignment line 28 on the +0.75 D converging plate 31 is aligned with the calibration line 11 on the power capsule 10 of retinoscope 1 as shown further in FIG. 8-A and secured 40.

With reference to FIG. 9-A, a retinoscope 1 having a +0.75 D converging plate 31 attached thereto is shown. The retinoscope 1 has been calibrated for a +0.75 D endpoint using converging retinoscopic light rays 14. The technique for performing retinoscopy using a retinoscope calibrated for a +0.75 D retinoscopic endpoint is the same as in conventional retinoscopy, except the calibration line 11 on power capsule 10 is aligned with the alignment line 28 on the +075 D converging plate 31 and the retinoscopic endpoint is a +0.75 D retinoscopic and moves in unison with the intercept.

Figures 10A, 11A:
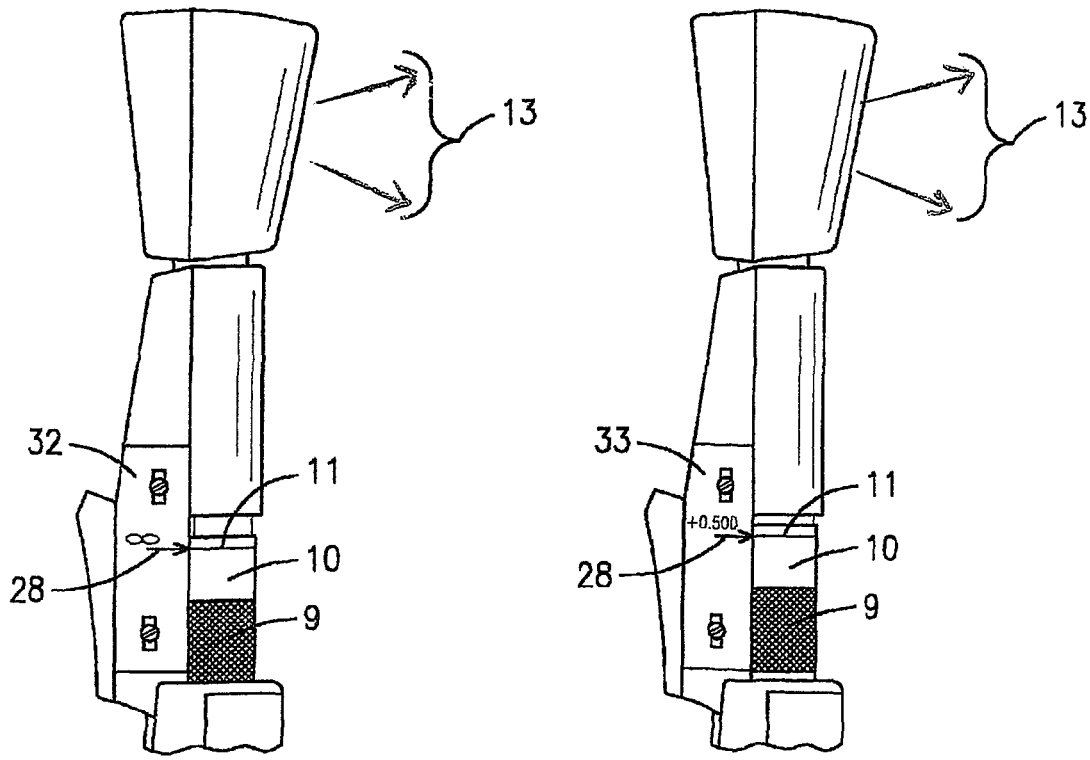
FIG. 10 is a flow chart showing the steps for calibrating a retinoscope for an infinity retinoscopic endpoint using diverging retinoscopic light rays calibrated to the examiner's retinoscopic working distance.
FIG. 11 is a flow chart showing the steps for calibrating a retinoscope for a +0.50 D retinoscopic endpoint using diverging retinoscopic light rays calibrated to the examiner's retinoscopic working distance.
Figure 10:
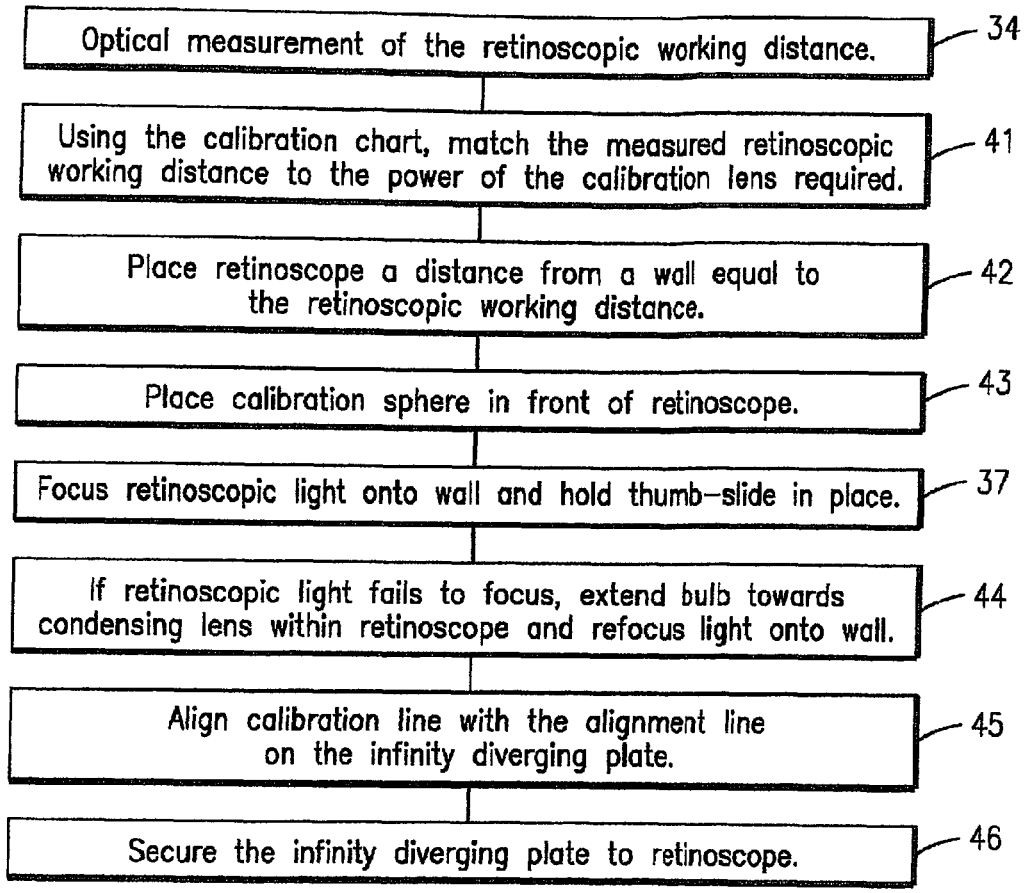

With reference to FIG. 10, a flow chart showing the steps for calibrating a retinoscope 1 for an infinity retinoscopic endpoint using diverging retinoscopic rays 13 is shown. First, the retinoscopic working distance 34 is measured in centimeters, as shown in FIG. 5. Next 41, the retinoscopic working distance in centimeters 19 is matched to the power of the calibration lens required 20 using the calibration chart 18. For example, if the retinoscopic working distance is 67 cm, the power of calibration sphere would be +3.00 D. Next, the retinoscope 1 is placed at a distance from the wall equal to the retinoscopic working distance 42. Next, the +3.00 D calibration sphere as determined from 41 is placed in front of the retinoscope 43. With the thumb-slide 2 in the maximal upward position and the diverging retinoscopic light shining through the +3.00 D calibration spherical lens, the thumb-slide 2 is lowered until the retinoscopic streak is focused onto the wall 37. If the retinoscopic streak fails to focus onto the wall, the bulb 4 is advanced towards the condensing lens 3 within the retinoscope 1 and the procedure repeated until the retinoscopic streak is focused onto the wall, 44. Next 45, the alignment line 28 on the infinity diverging plate 32 is aligned with the calibration line 11 on the power capsule 10 and secured in position 46 as shown further in FIG. 10-A.

With reference to FIG. 10-A, a retinoscope 1 having a diverging plate 32 attached thereto is shown. The retinoscope 1 has been calibrated for an infinity retinoscopic endpoint using diverging retinoscope light rays 13. The technique for performing retinoscopy using an infinity retinoscopic endpoint with the emitted retinoscopic light rays calibrated to the examiner's retinoscopic working distance is the same as in conventional retinoscopy, except that the calibration line 11 on the power capsule 10 is aligned with the measuring line 28 on the infinity plate 32.

Figure 11:
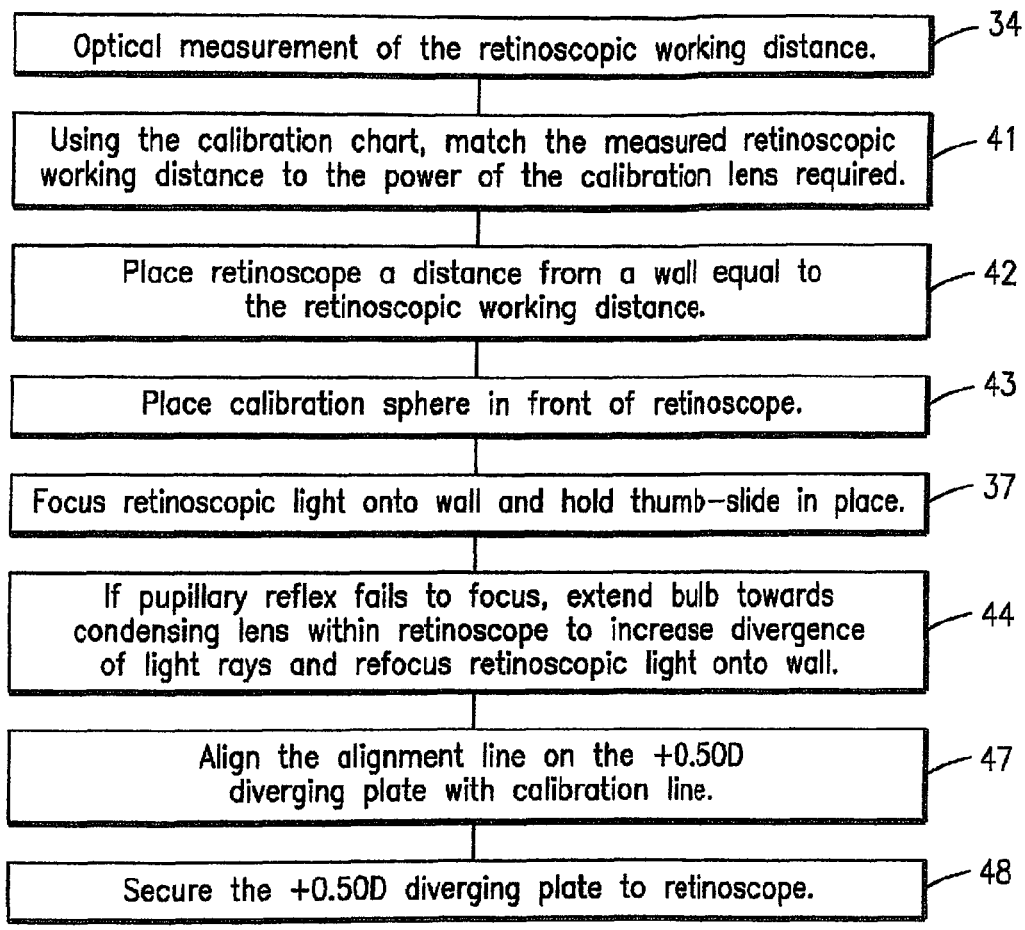

With reference to FIG. 11, a flow chart showing the steps for calibrating a retinoscope 1 for a +0.50 D retinoscopic endpoint using diverging retinoscope light rays 13 is show. First the working distance is measure centimeters 34, as shown in FIG. 5. Next 41, the retinoscopic working distance in centimeters 19 is matched to the power of the calibration lens required 21 using the calibration chart 18. For example, if the retinoscopic working distance is 67 cm the power of the calibration sphere would be +3.50 D. Next, the retinoscope 1 is placed at a distance from the wall equal to the retinoscopic working distance 42. Next, the +3.50 D sphere is placed in front of the retinoscope 43. With the thumb-slide 2 in the maximal upward position and the diverging retinoscopic light shining through the +3.50 D calibration lens, the thumb-slide 2 is lowered until the retinoscopic streak is focused onto the wall 37. If the retinoscopic streak fails to focus onto the wall, the bulb 4 is displaced toward the +20 D condensing lens 3 within the retinoscope and the procedure repeated until the retinoscopic streak is focused onto the wall, 44. Next 47, the alignment line 28 on +0.50 D diverging plate 33 is aligned with the calibration line 11 on the power capsule 10 and secured in position 48 as shown further in FIG. 11-A.

With reference to FIG. 11-A, a retinoscope 1 having a +0.50 D diverging plate 33 attached thereto is shown. The retinoscope 1 has been calibrated for a +0.50 D retinoscopic endpoint using diverging light rays 13 exiting the retinoscope. The technique for performing retinoscopy using a retinoscope calibrated to one's retinoscopic working distance for a +0.50 D retinoscopic endpoint is the same as conventional retinoscopy except the retinoscopic endpoint is a +0.50 D with-motion retinoscopic endpoint and the calibration line 11 is aligned with the alignment line 28. In contrast to the +0.50 D retinoscopic endpoint produced with converging rays emitted from the retinoscope in FIG. 8-A, with diverging rays the +0.50 D retinoscopic endpoint moves faster than the intercept.

Figure 12:
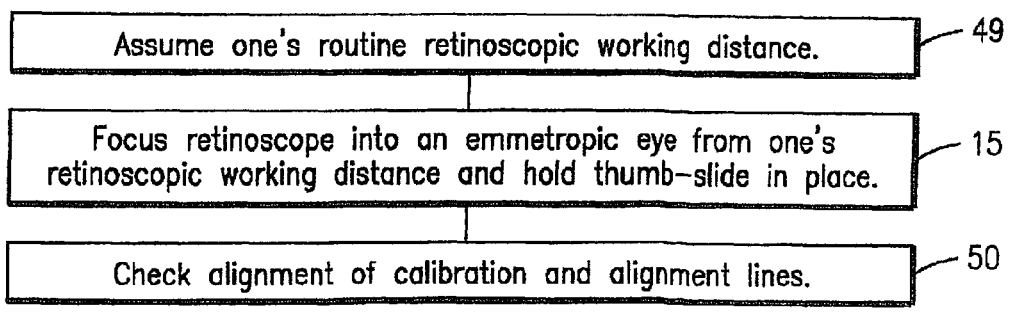
FIG. 12 is a flow chart showing the steps for performing a calibration check of a retinoscope emanating converging rays calibrated to the examiner's retinoscopic working distance.

With reference to FIG. 12, a flow chart showing the steps for performing a calibration check on retinoscopes calibrated to emit converging rays 14 as shown in FIGS. 8-A and 9-A is shown. First, the practitioner assumes his or her routine retinoscope distance 49. Then the practitioner lowers the thumb-slide 2 of the retinoscope from its maximal upward position until a neutrality reflex is seen in an emmetropic eye 12 and holds the thumb-slide in this position 15. If the calibration line 11 on the power capsule 10 is level with the alignment line 28 on the converging plates 25 or 31, the retinoscope is calibrated 50. In the Copeland Optec 360 Streak Retinoscope, the thumb-side is kept in the most superior position by a spring.

Figure 13:
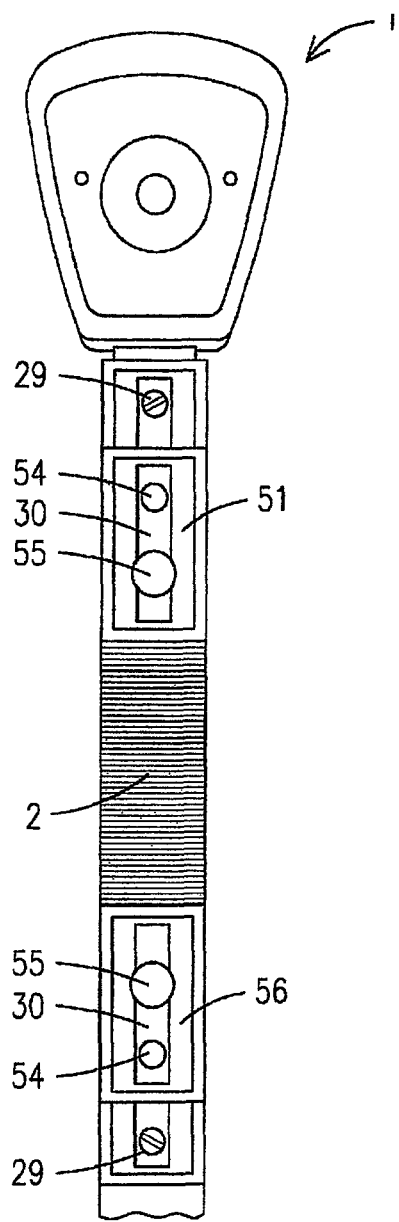
FIG. 13 is a rear view of a retinoscope showing a slide bar which can be adjusted to maintain the thumb-slide in a fixed position to maintain the calibration of the retinoscope for future retinoscopies.
Figure 14:
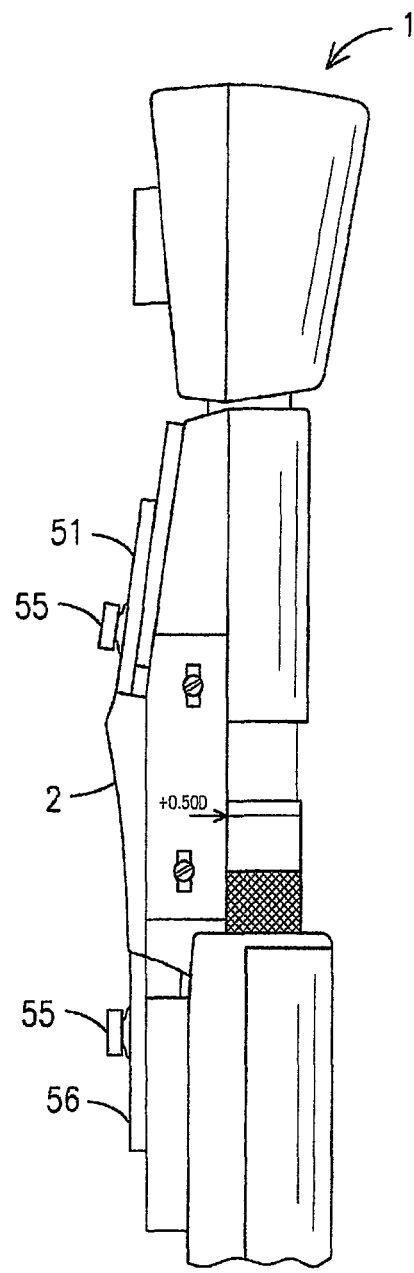
FIG. 14 is a side view of a retinoscope showing a slide bars which can be adjusted to maintain the thumb-slide in a fixed position to maintain the calibration of the retinoscope for future retinoscopies.

With reference to FIGS. 13 and 14, a rear view and a side view, respectively, of a retinoscope 1 having an upper slide bar 51 attached to the body of the retinoscope and located superiorly to the thumb-slide 2 thereto and having a lower slide bar 56 attached to the body of the retinoscope and located inferiorly to the thumb-slide 2 is shown. The slide bars 51, 56 are attachable to the retinoscope via an attachment means 29, such as screws, nut, etc. The slide bars 51, 56 are moveable via an adjustment means 30, such as a slot that moves along a post 54. After the retinoscope is calibrated, the slide bars 51, 56 are adjusted to touch the top and bottom, respectively, of the thumb-slide 2 and locked in place via a locking means 55, such as a screw, etc., to prevent the thumb-slide 2 from moving upward or downward.

Although a practitioner may use a +0.50 D retinoscopic endpoint or a +0.75 D retinoscopic endpoint, the +0.50 D retinoscopic endpoint is easier, faster and more convenient to confirm than the +0.75 D retinoscopic endpoint, since during retinoscopy, the neutrality reflex is displaced 2 lenses from the +0.50 D retinoscopic endpoint and 3 lenses from the +0.75 D retinoscopic endpoint.

Figure 15:
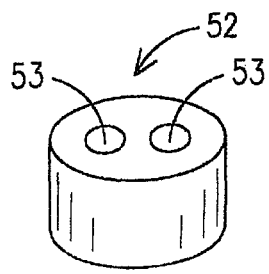
FIG. 15 is a front perspective view of a bulb extender of the present invention.
Figure 17:
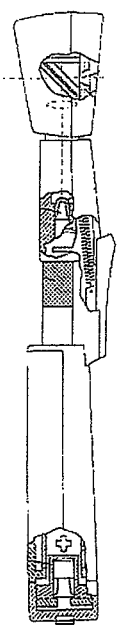
FIG. 17 is a side view of a retinoscope of the prior art.
Figure 18:
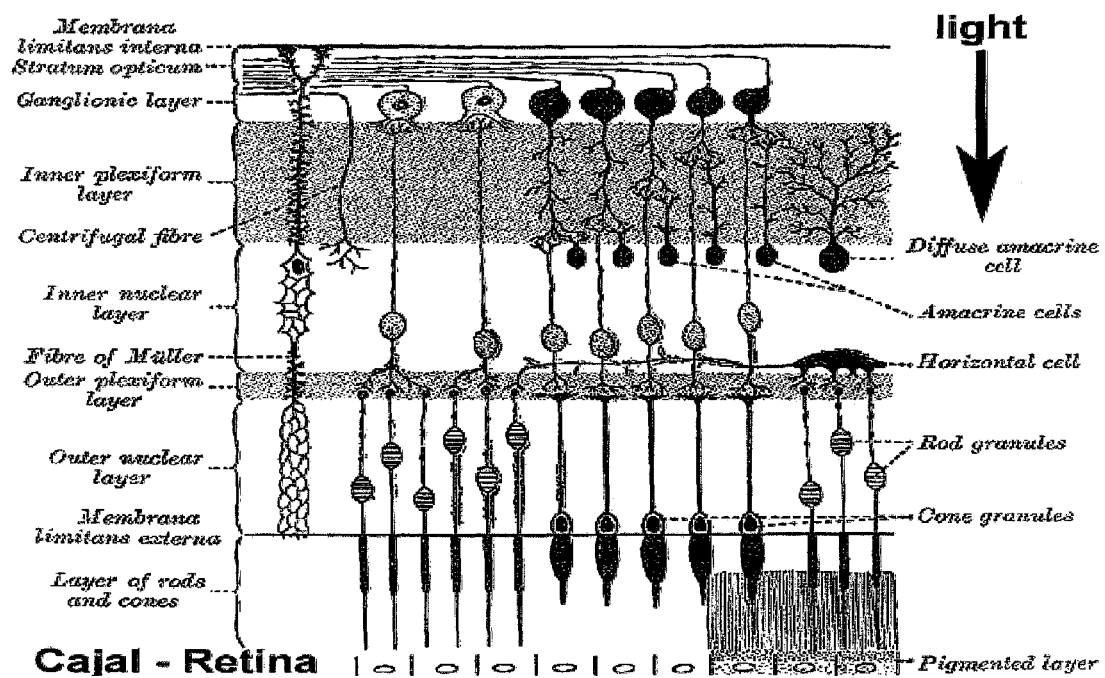
FIG. 18 is an illustration of histology of the macula with pigment epithelium.

Finally with reference to FIG. 15, a front perspective view of a bulb extender 52 of the present invention is shown. The bulb extender 52 acts as a spacer to increase the height of a lamp 4 and filament 5 within the retinoscope 1. The bulb extender 52 elevates lamps 4 having shorter filaments 5 towards the lens 3 to increase the divergence of emitted retinoscopic light. The bulb extender 52 has at least one aperture 53 to allow electronic communication between a power source of the retinoscope 1 and the filament 5.

Figure 19A:
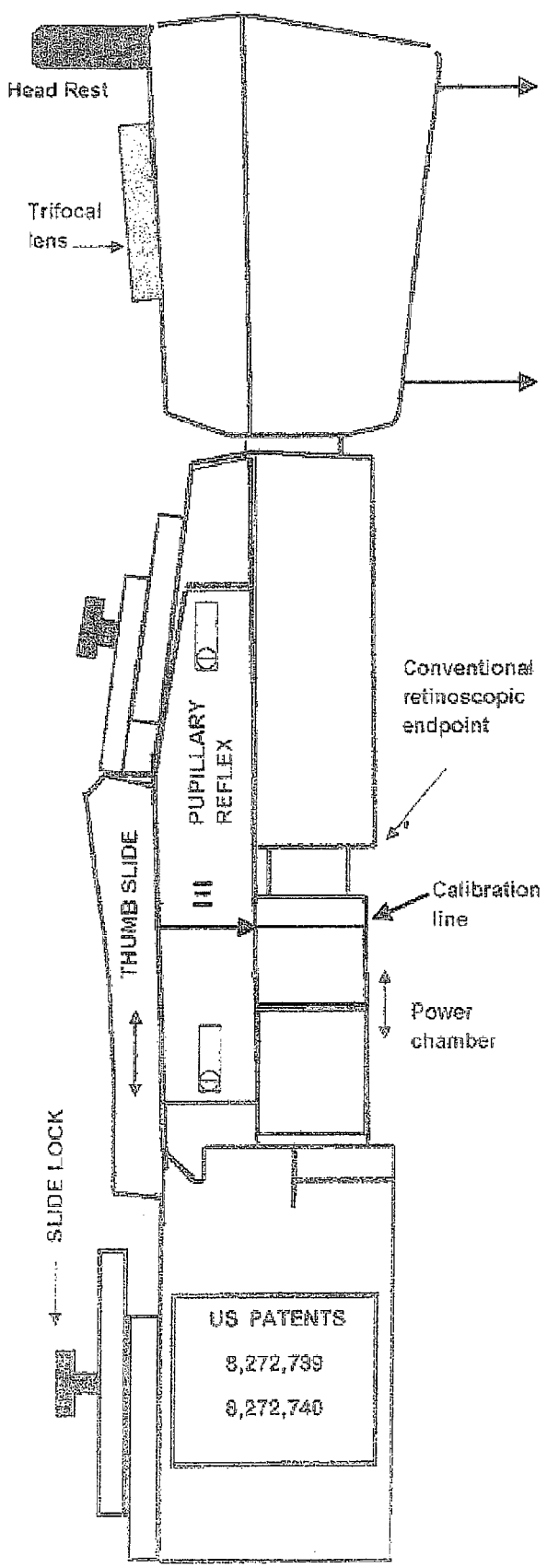
FIG. 19A is a side view of a retinoscope calibrated to emit parallel light rays to make the streak pupillary reflex image and the image seen by the examiner conjugate.
Figure 19B:
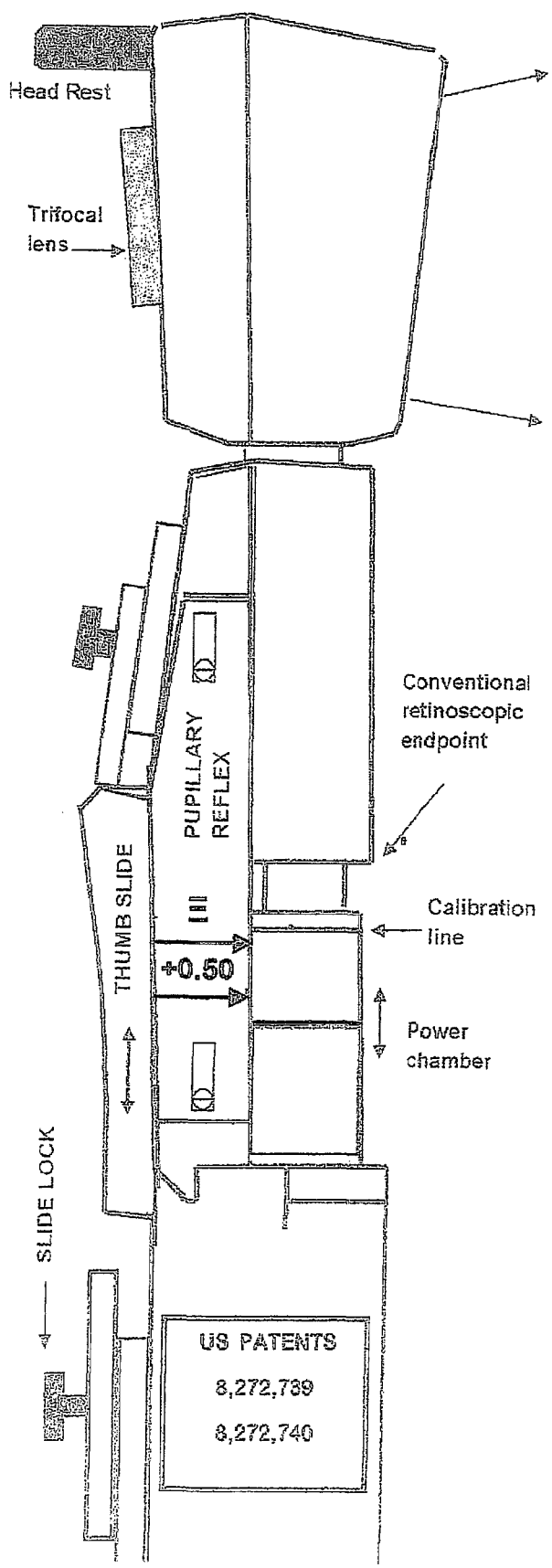
FIG. 19B is a side view of a retinoscope calibrated for converging retinoscopy with a +0.50 D pupillary streak endpoint and parallel retinoscopy for the detection of age-related maculopathies.
Figure 19C:
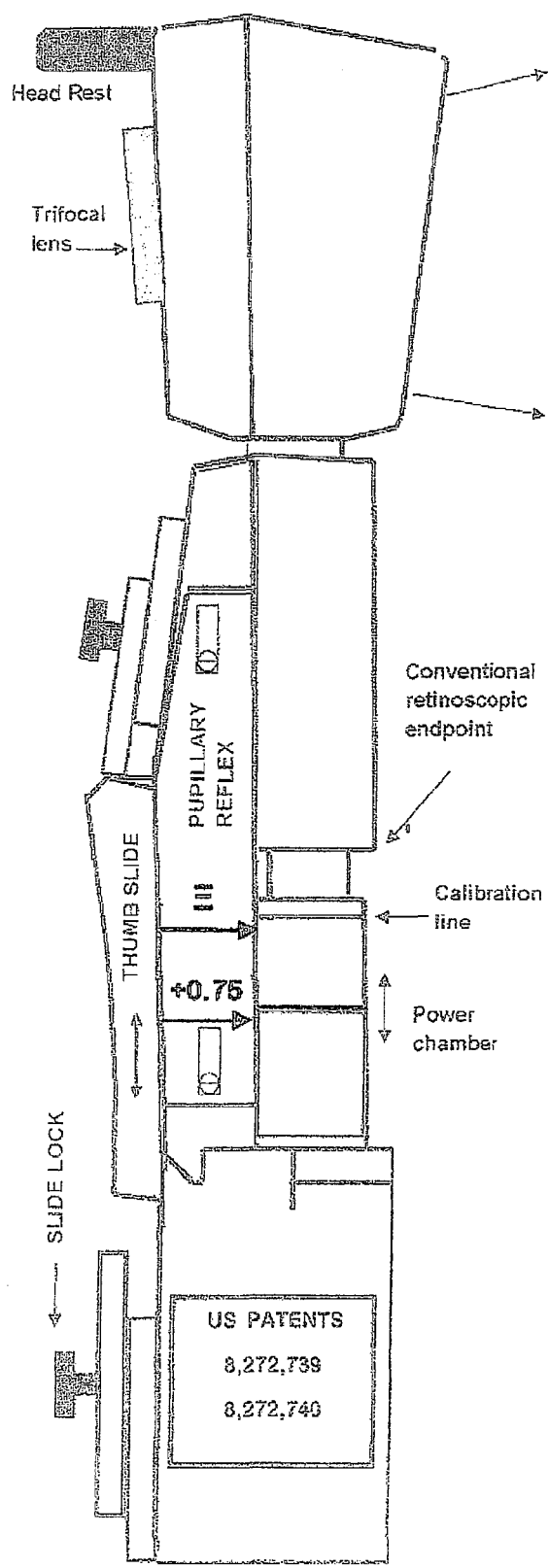
FIG. 19C is a side view of a retinoscope calibrated for converging retinoscopy with a +0.75 D pupillary streak endpoint and parallel retinoscopy for the detection of age-related maculopathies.
Figure 19D:
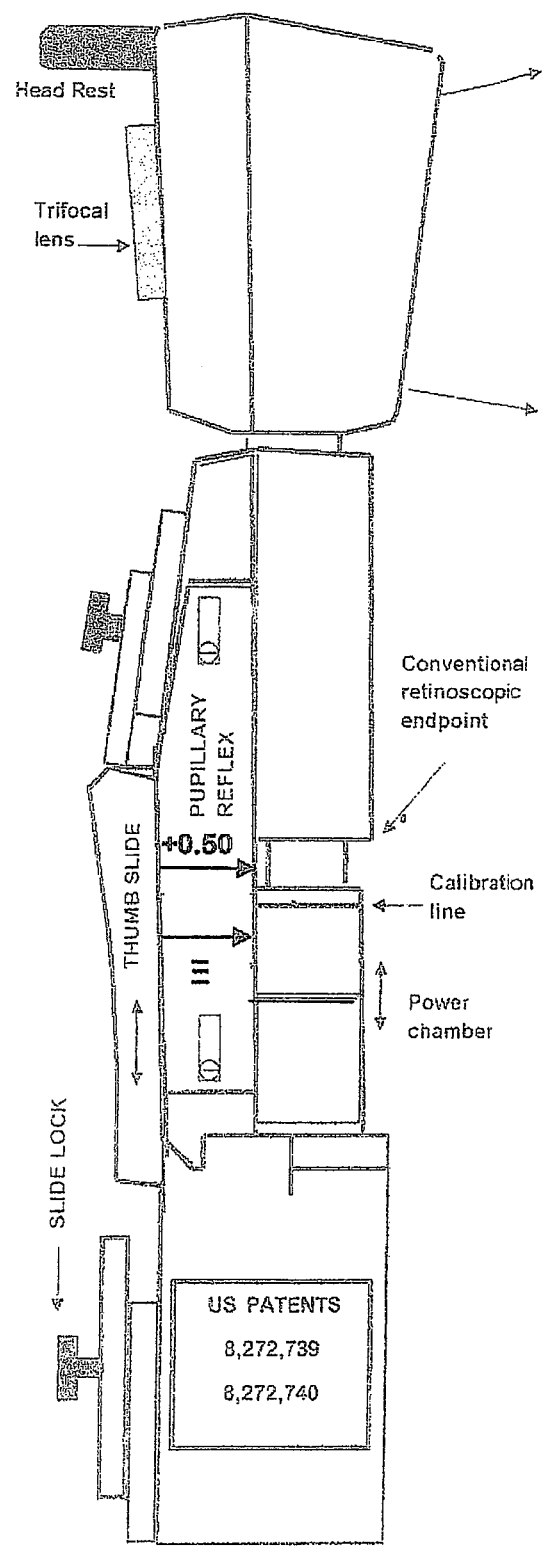
FIG. 19D is a side view of a retinoscope calibrated for diverging retinoscopy with a +0.50 D pupillary streak endpoint and parallel retinoscopy for the detection of age-related maculopathies.
Figure 19E:
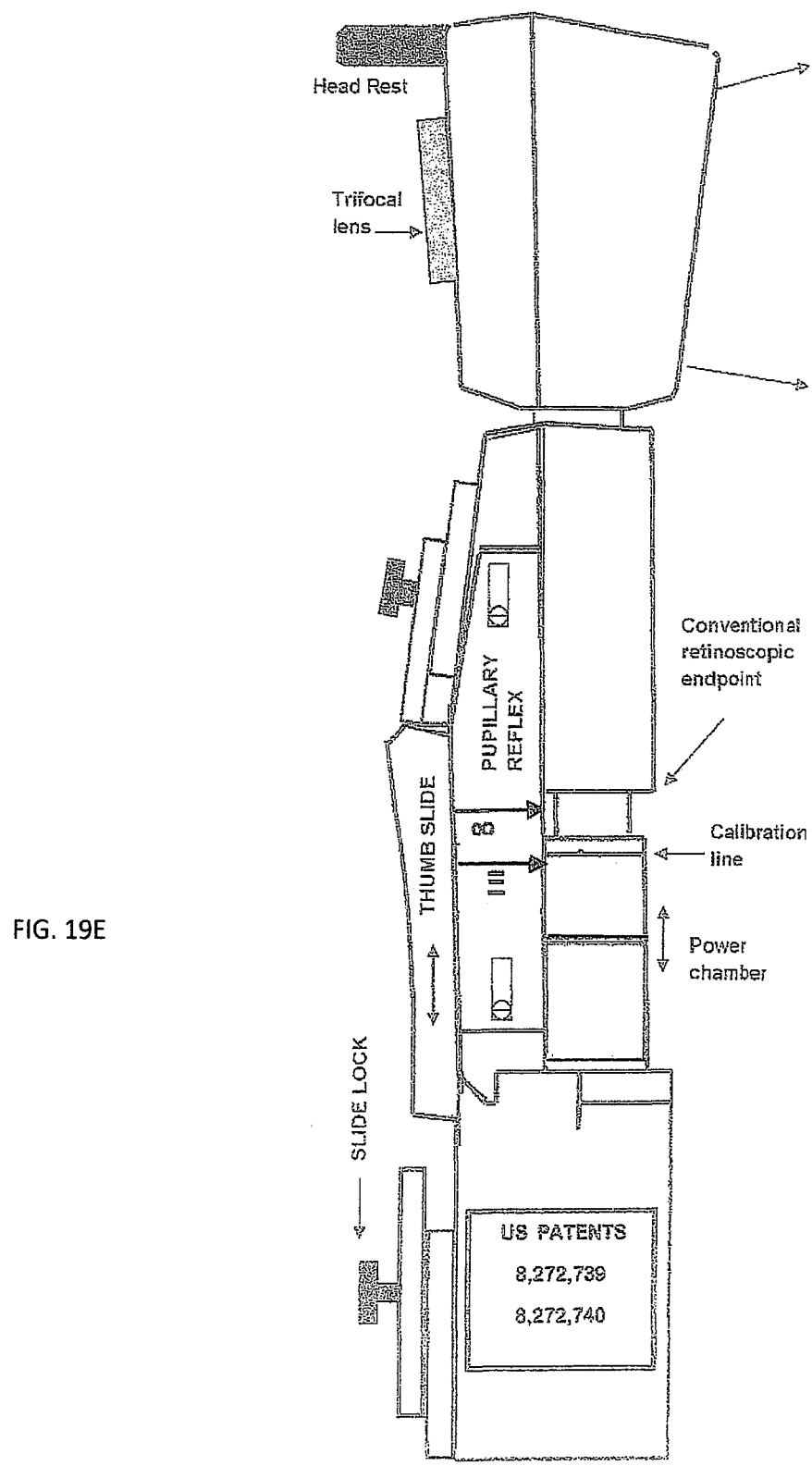
FIG. 19E is a side view of a retinoscope calibrated for diverging retinoscopy with an infinity neutrality pupillary endpoint and parallel retinoscopy for the detection of age-related maculopathies and having slide locks above and below the thumb slide to allow the examiner to change the divergence or convergence of the retinoscopic light to parallel light rays without moving the retinoscope.
Figure 20A:
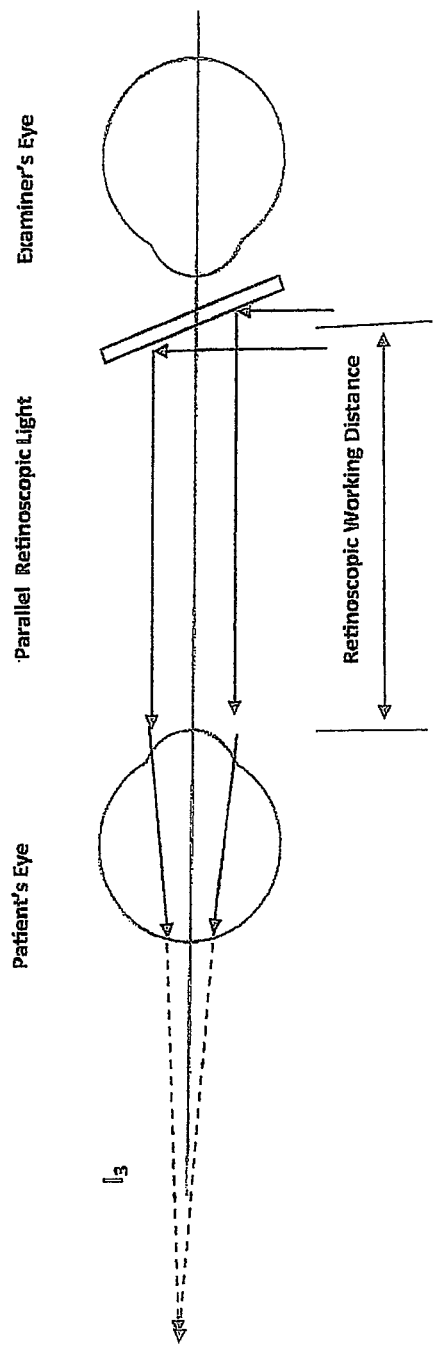
FIG. 20A is an illustration of an extrapolated focal point (Image $I_3$) behind a retina when the retinoscopic light is parallel (Image $I_1$=0.00 D)
Figure 20B:
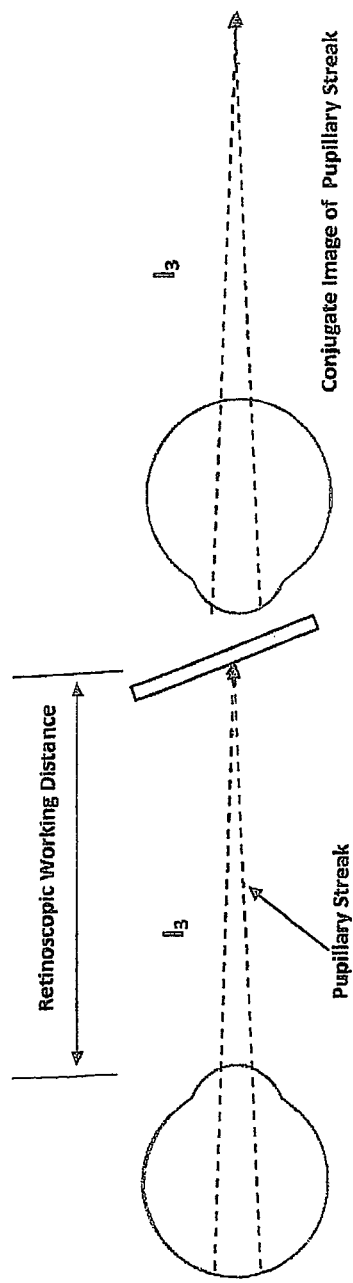
FIG. 20B is an illustration of a reflected pupillary image (Image $I_3$) focused to a hole in a mirror with the examiner seeing a reflected streak pupillary image (Image $I_3$) as a conjugate image.

With reference to FIGS. 19A-22, the measurement of the reflectance of the MPOD is preferably performed with a modified Copeland Optec 360 Streak Retinoscope, with a halogen or incandescence bulb with a linear filament and an elongated permanent or attachable head rest, as illustrated in FIG. 19A projecting parallel light rays. The thumb-slide moves the bulb in relation to a +20.0 D spherical lens within the retinoscope to emit parallel light. The slide locks maintains the retinoscope in calibration when performing retinoscopy with diverging, converging or parallel retinoscopic light (as illustrated in FIGS. 1-15). The retinoscopic technique for detecting AMD requires the retinoscope to emit parallel light rays from the same retinoscopic working distance for each eye.

Formula for Calibration of Retinoscope to Emit Parallel Light:

The formula for determining the focal length and power of the pupillary image of the retinoscope emitting parallel light is:

Image $I_1$+Image $I_3$=$t(D)$ at emmetropia

Image $I_1$=vergence of retinoscopic light($D$)

Image $I_3$=pupillary reflex($D$)

$t(D)$=RWD expressed in diopters

Since the vergence of parallel light (Image $I_1$) is 0.00 D, the pupillary reflex is equal to the retinoscopic working distance (cm) expressed in diopters.

Image $I_3$=$t(D)$ at emmetropia

Upon neutralization of the patient's refractive error and the fulfillment of the examiner's retinoscopic requirements, conjugate or identical images are formed in the patient's and an examiner's eyes.

Requirements for Examiner to See Conjugate Images of the Reflected Pupillary Streak (Image $I_3$)

1. The examiner's refractive error must be corrected.
2. If the retinoscopist is presbyopic, a spherical lens with a focal length equal to the retinoscopic working distance attached to the back of the retinoscope will produce a clear image of the pupillary streak.
3. The retinoscopic working distance must be the same for the right and left eyes.
4. The patient's right eye must be examined by the retinoscopist's right eye and vice versa.
5. The evaluation of the diagnostic pupillary streak requires an 8-10° off-axis retinoscopic position, laterally displaced. This allows the patient to fixate on the Snellen letters, reduces accommodation and maintains central fixation. An 8-10° off-axis position requires the retinoscope to be displaced 4 cm laterally to the patient's pupil for a 60-65 cm retinoscopic working distance.
6. The highest concentration of pigment 15 located in the fovea. The foveal pigment decreases precipitously by a factor of $\frac{1}{300}$, 7-8° from the foveal axis to the periphery of the retina (Beatty). A decrease in the 8-10° off axis reflectance of the pupillary reflex as compared to on-axis retinoscopy is more indicative of RPE damage and loss of melanin pigment of the retinal pigment epithelium.
7. A 3-4 mm undilated pupil produces the optimal conjugate pupillary reflex. A dilated pupil induces higher order aberrations blurring the optical qualities of the pupillary streak. A dilated pupil will induce aberrant astigmatic error in the pupillary reflex, especially in the vertical meridian.

Figure 21:
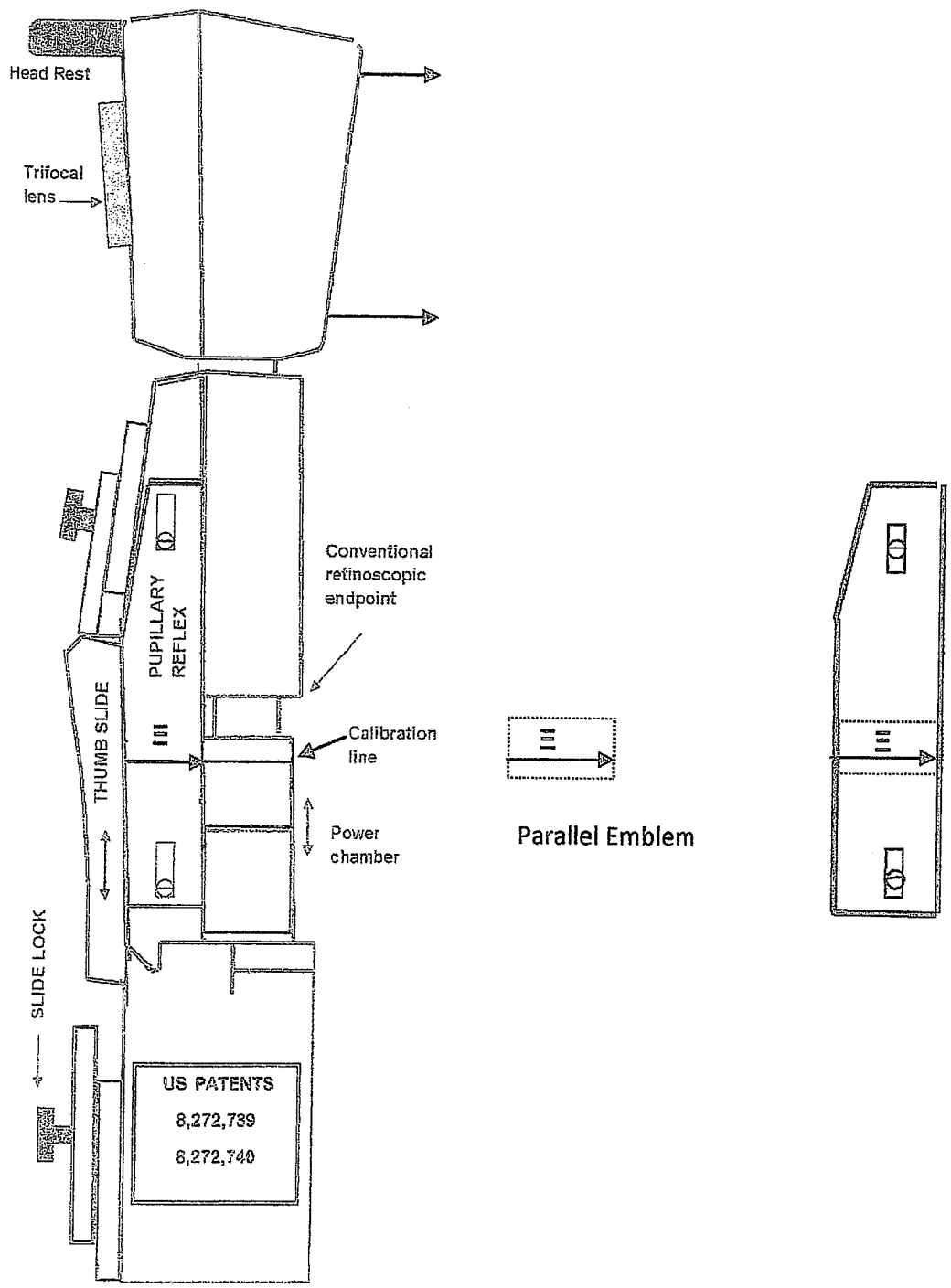
FIG. 21 is a side view of a retinoscope calibrated to emit parallel light and an attachable emblem having a parallel light line attached to the slide plate after calibration of the retinoscope.

Calibration of Retinoscope to Emit Parallel Light Rays:

1. Move the thumb-slide to focus the retinoscopic light through a spherical lens onto a wall displaced the focal length of the sphere from the wall. Adjust slide bars 51 and 56 to keep retinoscope calibrated emitting light.
2. Align the arrow head of the "parallel calibration line" Ξ symbol on the calibration plate or the attachable Ξ emblem in FIG. 21 with the circumferential calibration line above the knurl to mark the position of the power capsule housing the bulb for future parallel infinity retinoscopies.
4. Attach calibration plate to the side of the retinoscope, as illustrated in FIG. 21.
5. Adjust the slide-bar to maintain the thumb-slide in a fixed position to maintain the calibration of the retinoscope for future diagnostic parallel and converging or diverging retinoscopies, as illustrated in FIG. 19B-E. The thumb-slide and slide bars allows one to change the vergence of the retinoscopic light from converging or diverging retinoscopy to parallel without moving the retinoscope or changing the retinoscopic working distance.

The luminance of the calibrated pupillary streak is graded on a scale of 0-4, as illustrated in FIG. 22, to evaluate the severity of the age-related maculopathy or degeneration (AMD) and other maculopathies.

With reference to FIG. 19, a calibrated streak retinoscope for use with the Primary Scale is illustrated. The retinoscope has the following features:
1. Elongated head rest allows examiner to wear glasses in order to see the pupillary reflex clearly.
2. A trifocal lens is attached to the back of retinoscope for Presbyopic examiners.
3. Slide locks maintain calibration of the retinoscope as the thumb slide moves from calibrated converging or conventional retinoscopy to parallel for diagnostic retinoscopy,
4. Position for +0.50 D converging retinoscopy used in refractive retinoscopy.
5. Position for parallel retinoscopy ($\Xi$) used in diagnostic retinoscopy.

Using the Primary Scale in Diagnostic Retinoscopy

Diagnostic Retinoscopy is performed after a preliminary ophthalmic exam and a subjective refraction but prior to pupillary dilatation. The Diagnostic Retinoscopic Steps require:
1. The retinoscope, as illustrated in FIG. 1 to be calibrated to emit parallel light. Once calibrated, recalibration should be unnecessary. The brightness of the light should be evaluated often as the retinoscope is battery operated. The retinoscope may need to be re-calibrated if the bulb or the retinoscopic working distance (RWD) is changed.
2. The retinoscope is also calibrated for a +0.50 D pupillary streak endpoint (FIG. 1).
3. Slide locks allow the examiner to change the retinoscopic procedure from parallel retinoscopy to +0.50 D to converging retinoscopy by moving the thumb-slide without moving the retinoscope (FIG. 1).
4. An 8-10° off-axis retinoscopic position allows patients to read the Snellen chart thus maintaining foveal fixation. The 8-10° off-axis retinoscopic position allows the retinoscopic light to be focused onto the retina containing a high concentration of rods which surrounds the fovea.
5. The reflectance of the pupillary reflex is evaluated in the 180° meridian for consistency of comparison. The brightness of the 180° pupillary streak varies if the pupillary streak is rotated from the 0° meridian.

Figure 23:
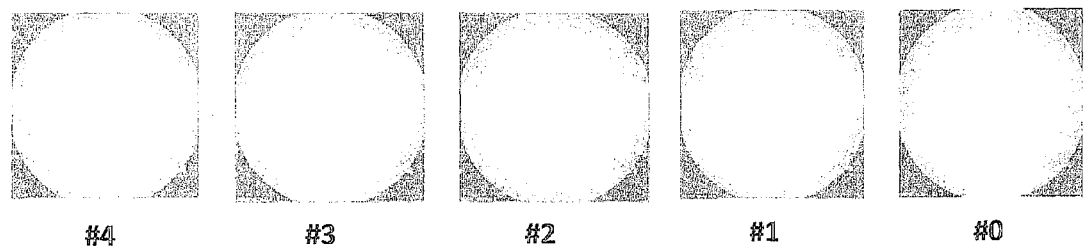
FIG. 23 is a pupillary streak brightness scale.

Primary Scale for Evaluating the Brightness of the Parallel ($\Xi$) Retinoscopic Pupillary Streak The brightness of the pupillary streak is graded on a scale of #0-#4, as illustrated in FIG. 23, with #4 being typical of young, healthy eyes to #0 which is typical in eyes with severe AMD.

After the parallel pupillary streak is evaluated and a notation made, the examiner will begin the evaluation of the pupillary streak using the Optical Scale, as illustrated in FIG. 22.

Figure 24:
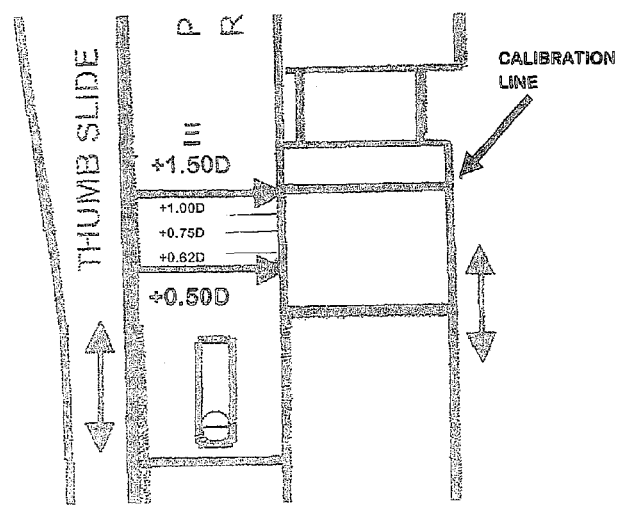
FIG. 24 is an illustration of power settings for calibrated converging retinoscopic settings (+1.50 D, +1.00 D, +0.75 D, +0.62 D and +0.50 D) expressed in diopters for a 67 cm RWD.

The retinoscope of the present invention allows a confirmation of the Primary Scale using a more Objective Scale comprised of four additional settings for converging light that are illustrated in FIG. 24. This is an important addition to the patent as it is more sensitive to the detection of early and advanced macular degeneration. By objectively confirming the initial Objective Scale, novice examiners will become more confident as they become more experienced.

The retinoscope and scale has been calibrated for a 65 cm retinoscopic working distance (RWD) and parallel light (+1.50 D) which produced the brightest pupillary streak and four converging retinoscopic settings (+1.00 D, +0.75 D+0.62 D and +0.50 D) which reduce the light intensity of reflected pupillary reflex by extending the focal lengths of the retinoscopic light. These positions are marked, as illustrated in FIG. 24, can be changed using the thumb slide. Decreasing the settings in this order renders a gradual reduction of the light intensity of the pupillary reflex seen by the examiner.

The scale illustrated in FIG. 24 represents the position of the linear bulb filament for a +20.00 D lens in the power chamber of the Copeland Streak Retinoscope for a 67 cm retinoscopic working distance (RWD) to produce the pupillary reflexes (+1.50 D to +0.50 D) of decreasing light intensity. If the RWD is not 67 cm. a different scale plate calibrated to the patient's RWD is attached to the handle of the retinoscope and adjusted, as illustrated in FIG. 19. The calibration scales in FIGS. 19 & 24 are based upon Formula 1 below.

$$\text{Image } I_1 + \text{Image } I_3 = t(D) \text{ at emmetropia} \quad (1)$$

Image $I_1$=vergence of retinoscopic light(D)

Image $I_3$=pupillary reflex(D)

$t(D)$=RWD expressed in diopters

The decrease in the illumination of the pupillary reflex in eye with AMD and similar maculopathies can be calculated using the chart in FIG. 25 since:
1. The linear height size of the retinoscopic light focused onto the retina and reflected as the pupillary streak is related to the total focal length of the retinoscopic light emitted from the retinoscope ($I_1$).
2. The intensity of radiant light energy from a point surface decreases in proportion to the distance from the object squared when there is no energy absorbed or scattered by the medium.
3. The decrease in the reflectance of the pupillary streak is indicative of the degree of RPE and photoreceptor degeneration in AMD and other various maculopathiesin eyes with clear media.

The decrease in the illumination of the pupillary reflex can be calculate since the intensity of radiant light energy from a point surface decreases in proportion to the distance from the object squared when there is no energy absorbed or scattered by the medium. The decrease in the reflectance of the pupillary streak is indicative of the degree of RPE and photoreceptor degeneration in AMD eyes with clear media.

Elongating the 67 cm focal length of the papillary reflex decreases the light intensity of the parallel pupillary streak, as illustrated in FIG. 25. The pupillary reflex produced with the Copeland Optec 360 Streak Retinoscope cannot be measured below a +0.50 D pupillary streak with the scale, as illustrated in FIG. 24, as the spacing between the dioptric powers becomes infinitely small.

Using the Optical Scale:

The scale on the retinoscope as illustrated in FIG. 24, allows one to evaluate the RPE and photoreceptor damage by comparing the brightness of the papillary reflex produced with parallel light emitted from the retinoscope to the brightness of the pupillary reflex produced by elongating the length of the papillary reflex from 67 cm to 200 cm (+0.50 D) to reduce the light intensity of the papillary reflex as illustrated in FIG. 25.

When the pupillary streak disappears, the position of the calibration line on the scale illustrated in FIG. 24 will be proportionate to the AMD damage. The papillary streak in a healthy eye remains visible as the light intensity of the papillary reflex is extended from 67 cm to 200 cm.

With Diagnostic Retinoscopy and estimating the degree of retinal degeneration, an ophthalmologist or optometrist can refer patients to a specialist prior to significant decreases in visual acuity, Amsler Grid distortions or severe retinal damage. These techniques could improve the diagnostic skills of physicians in early detection of AMD and screenings could be part of every eye examination. Early detection will greatly benefit patients, research and society.

It is to be understood that while a preferred embodiment of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

Having thus described my invention, I claim:

1. A system for calibrating a retinoscope for detecting age-related maculopathies, said retinoscope having a handle, a lamp housed within a power capsule with a calibration line located thereon, a lens located above the lamp, a thumb-slide for sliding the power capsule housing the lamp up or down, a calibration plate slidably attached to a side portion of the retinoscope proximate to the thumb-slide, said calibration plate being constructed from a flat piece of material having a front surface and a rear surface with at least one parallel calibration line located on the front surface; said system comprising:
a measurement of one's retinoscopic working distance using the retinoscope;
the retinoscope being calibrated to emit parallel light rays;
the parallel calibration line being aligned on the calibration plate with the calibration line on the power capsule; and
the retinscope calibrated to emit parallel light rays being placed at one measured retinoscopic working distance.

2. The system of claim 1 wherein:
said retinoscopic light is a parallel retinoscopic light.

3. The system of claim 1 wherein:
A head rest of the retinoscope is elongated to allow an examiner to wear glasses while using the retinoscope.

4. The system of claim 1 wherein:
maculapothies of the eye are detected.

5. The system of claim 1 wherein:
cystoid macular edema post cataract surgery is detected.

6. The system of claim 1 further comprising:
intensity of a chosen pupillary streak is reduced by a focal length of the retinoscopic light with the retinoscope being increased.

7. The system of claim 1 further comprising:
brightness of the a pupillary streak is graded on a primary scale.

8. The system of claim 7 further comprising:
the grade determined on the primary scale using an objective scale is confirmed.

* * * * *